United States Patent
Dwork

(10) Patent No.: US 9,492,275 B2
(45) Date of Patent: Nov. 15, 2016

(54) TRANSCATHETER PROSTHETIC HEART VALVE DELIVERY SYSTEM AND METHOD WITH EXPANDABLE STABILITY TUBE

(71) Applicant: Medtronic, Inc., Minneapolis, MN (US)

(72) Inventor: Joshua Dwork, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 145 days.

(21) Appl. No.: 13/905,632

(22) Filed: May 30, 2013

(65) Prior Publication Data

US 2013/0282111 A1  Oct. 24, 2013

Related U.S. Application Data

(62) Division of application No. 12/762,566, filed on Apr. 19, 2010, now Pat. No. 8,465,541.

(51) Int. Cl.
*A61F 2/24* (2006.01)
*A61F 2/966* (2013.01)

(52) U.S. Cl.
CPC ........... *A61F 2/2436* (2013.01); *A61F 2/2412* (2013.01); *A61F 2/2418* (2013.01); *A61F 2002/9665* (2013.01)

(58) Field of Classification Search
CPC ................... A61F 2/962; A61F 2/966; A61F 2002/9665; A61F 2/2436
USPC ............................. 623/1.11, 1.12, 2.11–2.42
See application file for complete search history.

(56) References Cited

U.S. PATENT DOCUMENTS

| | | | |
|---|---|---|---|
| 5,683,451 A | 11/1997 | Lenker et al. | |
| 5,713,949 A | 2/1998 | Jayaraman | |
| 5,824,041 A | 10/1998 | Lenker et al. | |
| 5,906,619 A | 5/1999 | Olson et al. | |
| 6,676,693 B1* | 1/2004 | Belding | A61F 2/95 606/108 |
| 2003/0065375 A1* | 4/2003 | Eskuri | 623/1.11 |
| 2005/0080430 A1* | 4/2005 | Wright et al. | 606/108 |
| 2005/0209671 A1 | 9/2005 | Ton et al. | |
| 2006/0265056 A1 | 11/2006 | Nguyen et al. | |
| 2007/0043420 A1* | 2/2007 | Lostetter | A61F 2/95 623/1.11 |
| 2007/0088431 A1 | 4/2007 | Bourang et al. | |
| 2007/0239266 A1 | 10/2007 | Birdsall | |
| 2007/0239269 A1 | 10/2007 | Dolan et al. | |
| 2009/0171456 A1 | 7/2009 | Kveen et al. | |

FOREIGN PATENT DOCUMENTS

| | | |
|---|---|---|
| WO | WO00/76425 | 12/2000 |
| WO | WO2009/091509 | 7/2009 |

* cited by examiner

Primary Examiner — Thomas McEvoy

(57) ABSTRACT

A device for percutaneously delivering a stented prosthetic heart valve. The device includes an inner shaft assembly, a delivery sheath assembly, an outer stability tube, and a handle. The sheath assembly is slidably disposed over the inner shaft, and includes a capsule and a shaft. The capsule compressively contains the prosthesis over the inner shaft. The stability tube is slidably disposed over the delivery sheath, and includes a distal region configured to be radially expandable from a first shape having a first diameter to a second shape having a larger, second diameter. In a first delivery state, the distal region assumes the first shape, providing a low profile appropriate for traversing a patient's vasculature. In a second delivery state, the distal region has the expanded diameter second shape, sized to receive the capsule, such as when retracting the capsule to implant the prosthesis.

14 Claims, 20 Drawing Sheets

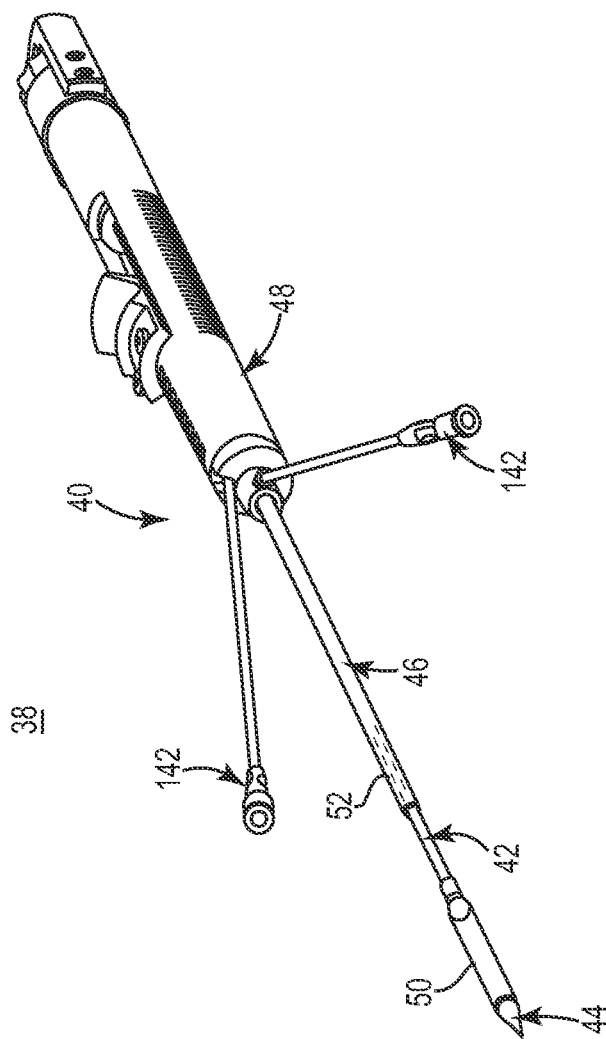

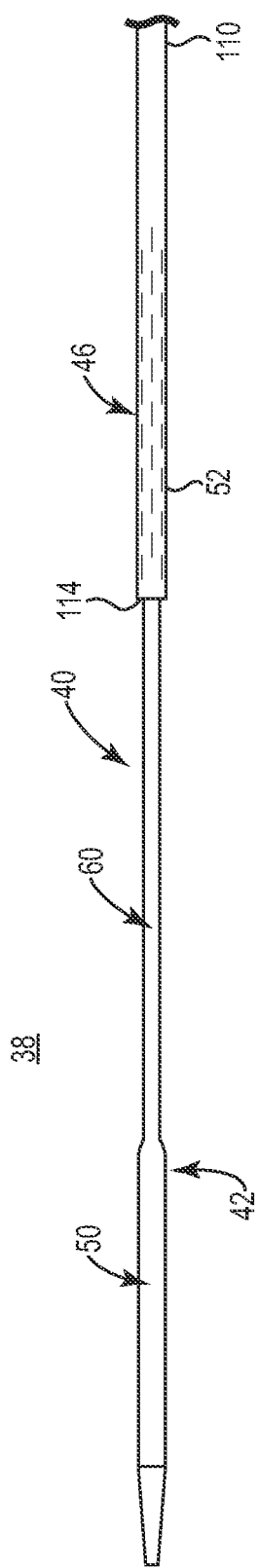
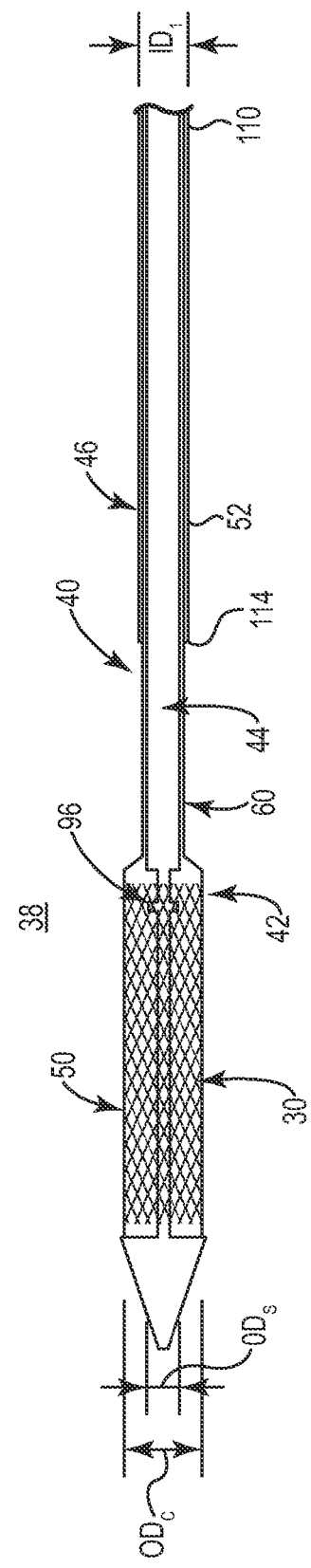
Fig. 7A
Fig. 7B

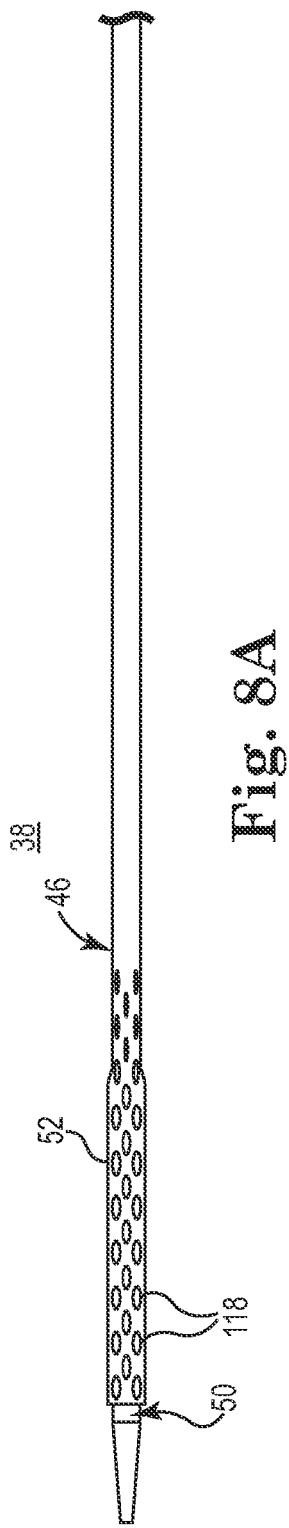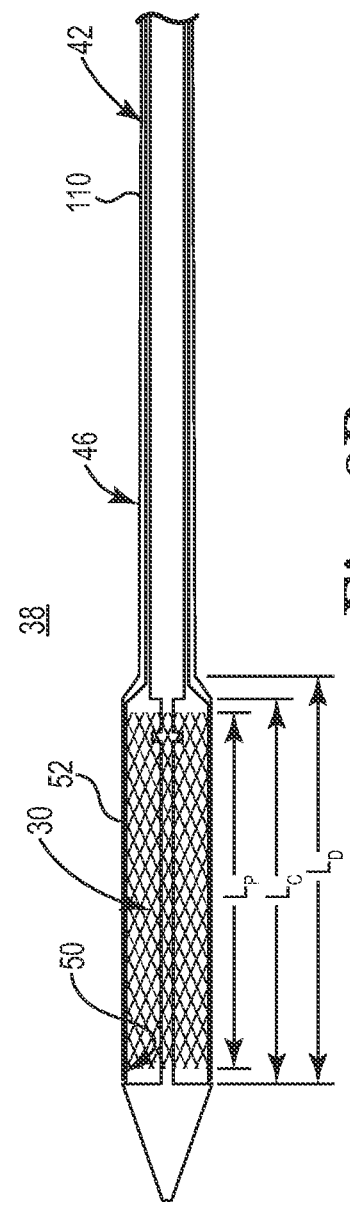

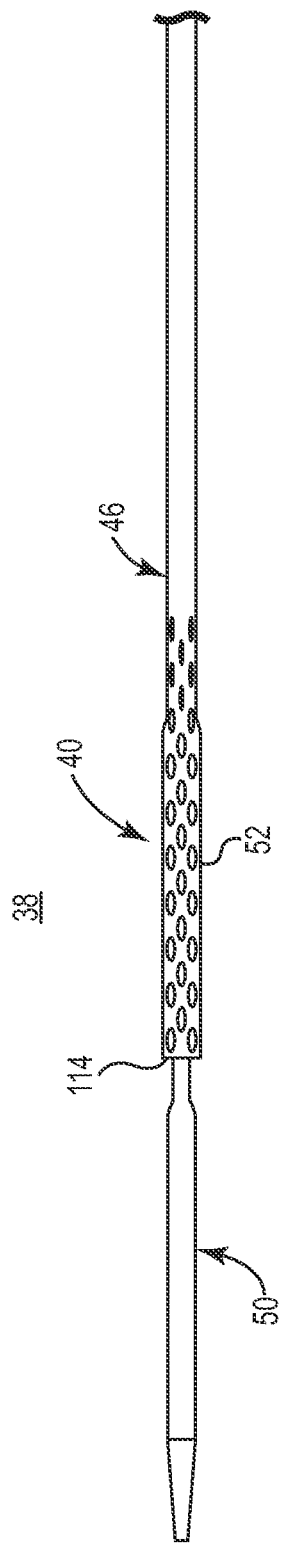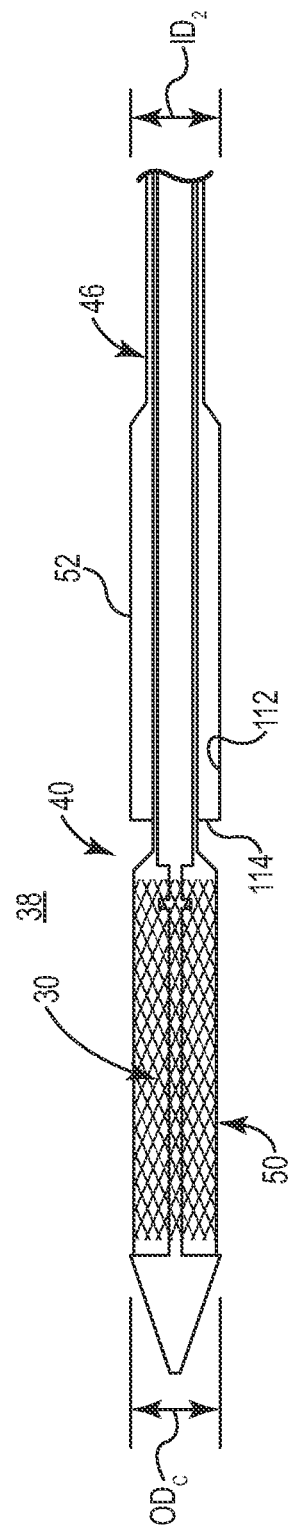

TRANSCATHETER PROSTHETIC HEART VALVE DELIVERY SYSTEM AND METHOD WITH EXPANDABLE STABILITY TUBE

RELATED APPLICATIONS

This application is a Division of and claims the benefit of U.S. patent application 12/762,566 filed Apr. 19, 2010. The disclosures of which are herein incorporated by reference in their entirety.

BACKGROUND

The present disclosure relates to systems and methods for percutaneous implantation of a stented structure, such as a stented prosthetic heart valve. More particularly, it relates to systems and methods for transcatheter implantation of a stented prosthetic heart valve.

Diseased or otherwise deficient heart valves can be repaired or replaced with an implanted prosthetic heart valve. As used through this specification, the terms "repair," "replace," and "restore" are used interchangeably, and reference to "restoring" a defective heart valve is inclusive of implanting a prosthetic heart valve that renders the native leaflets non-functional, or that leaves the native leaflets intact and functional. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a catheter-based delivery device and then advanced, for example, through an opening in the femoral artery and through the descending aorta to the heart, where the prosthesis is then deployed in the annulus of the valve to be repaired (e.g., the aortic valve annulus). Although transcatheter techniques have attained widespread acceptance with respect to the delivery of conventional stents to restore vessel patency, only mixed results have been realized with percutaneous delivery of the more complex prosthetic heart valve.

Various types and configurations of prosthetic heart valves are available for percutaneous valve replacement procedures, and continue to be refined. The actual shape and configuration of any particular transcatheter prosthetic heart valve is dependent to some extent upon the native shape and size of the valve being replaced or repaired (i.e., mitral valve, tricuspid valve, aortic valve, or pulmonary valve). In general, prosthetic heart valve designs attempt to replicate the functions of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation devices, the stent frame of the valved stent is made of a self-expanding material and construction. With these delivery devices, the valved stent is crimped down to a desired size and held in that compressed arrangement within an outer delivery sheath, for example. Retracting the sheath from the valved stent allows the stent to self-expand to a larger diameter, such as when the valved stent is in a desired position within a patient. In other percutaneous implantation devices, the valved stent can be initially provided in an expanded or uncrimped condition, then crimped or compressed on a balloon portion of a catheter until it is as close to the diameter of the catheter as possible. The so-loaded balloon catheter is slidably disposed within an outer delivery sheath. Once delivered to the implantation site, the prosthesis is removed from the delivery sheath and the balloon is inflated to deploy the prosthesis. With either of these types of percutaneous stented prosthetic valve delivery devices, conventional sewing of the prosthesis to the patient's native tissue is typically not necessary.

In addition to the delivery device itself, typical transcatheter heart valve implantation techniques entail the use of a separate introducer device to establish a portal to the patient's vasculature (e.g., femoral artery) and through which the prosthetic heart valve-loaded delivery device is inserted. The introducer device generally includes a relatively short sheath and a valve structure. By inserting the prosthesis-containing delivery sheath through the introducer valve and sheath, a low-friction hemostasis seal is created around the outer surface of the delivery sheath. While highly desirable, friction between the introducer device and the delivery sheath can be problematic, leading to unexpected movement of the prosthesis prior to release from the delivery device.

In particular, with a self-expanding stented prosthetic heart valve, the outer delivery catheter or sheath is retracted from over the prosthesis, thereby permitting the stented valve to self-expand and release from the delivery device. Friction between the introducer device and the delivery sheath has a tendency to resist necessary proximal movement of the delivery sheath. Because the retraction force is initiated at a handle of the delivery device, this resistance is transferred to the handle. As a result, unless the clinician (and/or an assistant) carefully holds both the handle and the introducer device in a fixed position relative to one another throughout the deployment operation, the handle has a tendency to draw forward. This movement, in turn, is transferred onto the delivery device component (e.g., an internal shaft) otherwise coupled to the loaded prosthetic heart valve, potentially moving the internal component device (including the loaded prosthetic heart valve) forward or distally within the patient. While unintended, even a slight displacement from the expected deployment location of the prosthesis relative to the native annulus can lead to severe complications as the prosthesis must intimately lodge and seal against the native annulus for the implantation to be successful. If the deployed prosthesis is incorrectly positioned relative to the native annulus, the deployed stented valve may leak or even dislodge from the implantation site.

For example, FIG. 1A illustrates, in simplified form, an introducer device 10 establishing a portal to a patient's vasculature 12, and through which a prosthetic heart valve-loaded delivery shaft 14 (the tip of which is visible in FIG. 1A) has been inserted. As shown, the delivery shaft 14 has been manipulated to locate the loaded prosthetic heart valve 16 (referenced generally) in a desired position relative to an aortic valve 18. An outer delivery sheath 20 contains the prosthesis 16. Thus, in the state of FIG. 1A, the prosthetic heart valve 16 is properly positioned for deployment from the delivery shaft 14 upon proximal retraction of the delivery sheath 20 relative thereto, with a spacing S being established between a distal end of the delivery device's handle 22 and the introducer device 10. As shown in FIG.

1B, an actuator 24 of the handle 22 is moved by the clinician in an attempt to proximally pull or retract the delivery sheath 20 and release the prosthesis 16. Frictional interface between the delivery sheath 20 and the introducer device 10 may resist proximal movement of the delivery sheath 20 (conventionally, the introducer device 10 is held stationary). As a result, the handle 22 is instead pulled forward toward the introducer device 10 (reflected in FIG. 1B by a decrease in the spacing S). In effect, the handle 22 is being advanced over the delivery sheath 20 rather than the delivery sheath 20 being retracted into the handle 22. Forward movement of the handle 22 is, in turn, directed onto the delivery shaft 14, causing the delivery shaft 14 to distally advance (represented by the arrow B in FIG. 1B) and displace the deploying prosthetic heart valve 16 from the desired valve implantation site 18. While it may be possible to provide an additional isolation layer between the introducer device 10 and the delivery sheath 20, distinct constraints render implementation of an additional layer highly problematic. For example, the tortuous nature of the patient's vasculature necessitates that the delivery device have as low a profile as possible, thereby limiting an available size of the additional layer. Conversely, any additional layers must account for and facilitate necessary retraction of the delivery sheath 20 during a deployment operation.

In light of the above, although there have been advances in percutaneous valve replacement techniques and devices, there is a continued desired to provide different delivery devices for delivering cardiac replacement valves, and in particular self-expanding, stented prosthetic heart valves to an implantation site in a minimally invasive and percutaneous manner.

SUMMARY

Some aspects of the present disclosure relate to a delivery device for percutaneously delivering a radially self-expandable stented prosthetic heart valve. The delivery device includes an inner shaft assembly, a delivery sheath assembly, an outer stability tube, and a handle. The inner shaft assembly includes a coupling structure configured to selectively engage the prosthetic heart valve. The delivery sheath assembly is slidably disposed over the inner shaft assembly and includes a distal capsule and a proximal shaft. The capsule is configured to compressively contain the prosthetic heart valve in a compressed arrangement. The outer stability tube is slidably disposed over the delivery sheath assembly, and includes a proximal region and a distal region. The distal region includes a tubular wall having a plurality of cuts formed through a thickness thereof. Further, the distal region is configured to be radially expandable from a first shape having a first diameter to a second shape having a larger, second diameter. The handle includes a housing and is operable to selectively move the delivery sheath assembly relative to the inner shaft assembly and the stability tube. The delivery device is configured to provide a first delivery state in which the distal region of the stability tube is proximal the capsule and assumes the first shape. In a deployed state, the capsule is at least partially withdrawn into the distal region and the distal region assumes the second shape. With this construction, in the delivery state, the delivery device has a relatively low profile appropriate for traversing a patient's vasculature, such as across the aortic arch. Further, the stability tube can be located in close proximity to the capsule to provide enhanced stabilization.

Yet other aspects of the present disclosure relate to a system for restoring a defective heart valve of a patient. The system includes a prosthetic heart valve and the delivery device as described above. The prosthetic heart valve includes a stent frame and a valve structure attached to the frame and forming at least two valve leaflets. In this regard, the prosthetic heart valve is radially self-expandable from a compressed arrangement to a normal, expanded arrangement. Upon assembly of the system to a delivery condition, the capsule compressively contains the prosthetic heart valve in the compressed arrangement over the inner shaft assembly. The system can be transitioned to a deployed condition in which a capsule is retracted from the prosthetic heart valve and at least partially into the distal region to permit the prosthesis to self-deploy toward the normal arrangement and release from the delivery device. With respect to the delivery condition, the delivery device includes or provides the first and second states as described above, including the distal region of the stability tube transitioning from the smaller diameter first shape to the larger diameter second shape. In some embodiments, a length of the distal region is greater than a length of the prosthetic heart valve.

Yet other aspects in accordance with the present disclosure relate to a method of restoring a defective heart valve of the patient. The method includes receiving a delivery device loaded with a radially self-expandable prosthetic heart valve having a stent frame to which a valve structure is attached. The delivery device includes a delivery sheath having a capsule extending distally from a shaft and containing the prosthetic heart valve in a compressed arrangement in a loaded state of the delivery device. The delivery device further includes an outer stability tube coaxially received over the delivery sheath and including a distal region terminating at a distal end located proximal the capsule and defining a first shape having a first diameter. The distal region includes a tubular wall having a plurality of cuts through a thickness thereof. The prosthetic heart valve is delivered, in the compressed arrangement, through a bodily lumen of the patient to an implantation site of the defective valve via the delivery device. The capsule is proximally retracted from over the prosthetic heart valve and at least partially into the distal region of the stability tube, allowing the prosthetic heart valve to self-deploy from the delivery device and implant within the defective valve. In this regard, the distal region assumes a second shape having an increased diameter for receiving the capsule. In some embodiments, prior to proximal retraction of the capsule, the distal region of the stability tube is forced to expand from the first shape to the second shape. In related embodiments, the distal region of the stability tube is forced to expand to the second shape by distally advancing the distal region over the capsule such that the capsule exerts an internal expansive force upon the distal region, thereby causing the distal region to transition from the first shape to the second shape. The stability tube is then moved proximally, retracting the distal region from the capsule. Upon retraction from the capsule, the distal region self-maintains the second shape in some constructions and is thus appropriately sized to slidably receive the capsule upon retraction of the delivery sheath in deploying the prosthetic heart valve.

BRIEF DESCRIPTION OF THE DRAWINGS

FIG. 3 is a perspective view of a system for restoring (e.g., replacing) a defective heart valve of a patient, including the prosthetic heart valve of FIG. 2A and a delivery device in accordance with principles of the present disclosure;

FIG. 7A is a simplified side view of a portion of the system of FIG. 3 in a delivery condition including the delivery device of FIG. 4 loaded with the prosthetic heart valve of FIG. 2B and in a first delivery state;

FIG. 7B is a simplified, cross-sectional view of the system of FIG. 7A;

FIG. 8A is a simplified side view of the system of FIG. 7A in an intermediate stage of operation;

FIG. 8B is a side, cross-sectional view of the system of FIG. 8A;

FIG. 9A is a simplified side view of the system of FIG. 7A and including the delivery device a second delivery state;

FIG. 9B is a side cross-sectional view of the system of FIG. 9A;

DETAILED DESCRIPTION

Figure 1A:
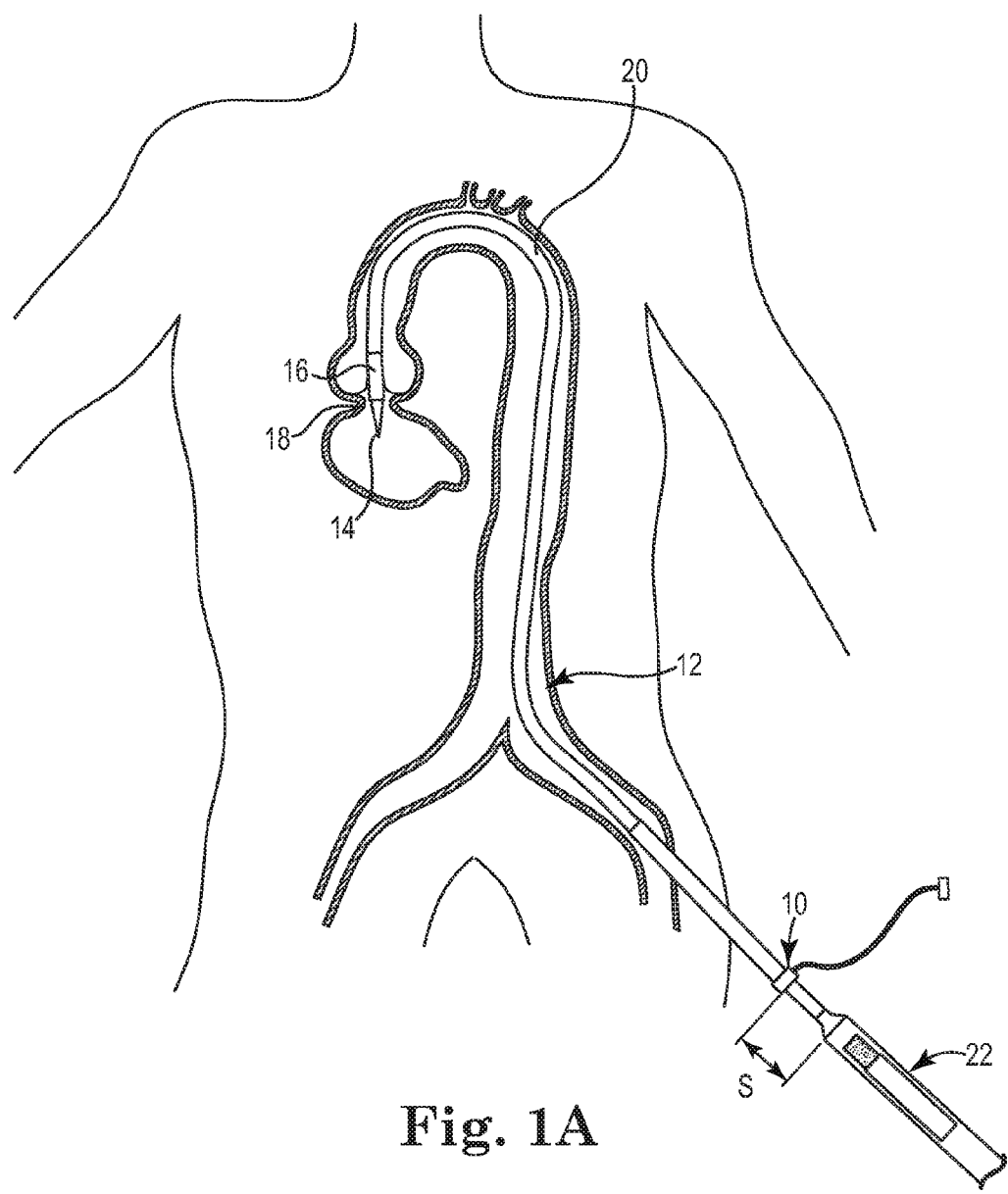
FIGS. 1A and 1B are simplified illustrations of conventional transcatheter delivery and implantation of a stented prosthetic heart valve.
Figure 1B:
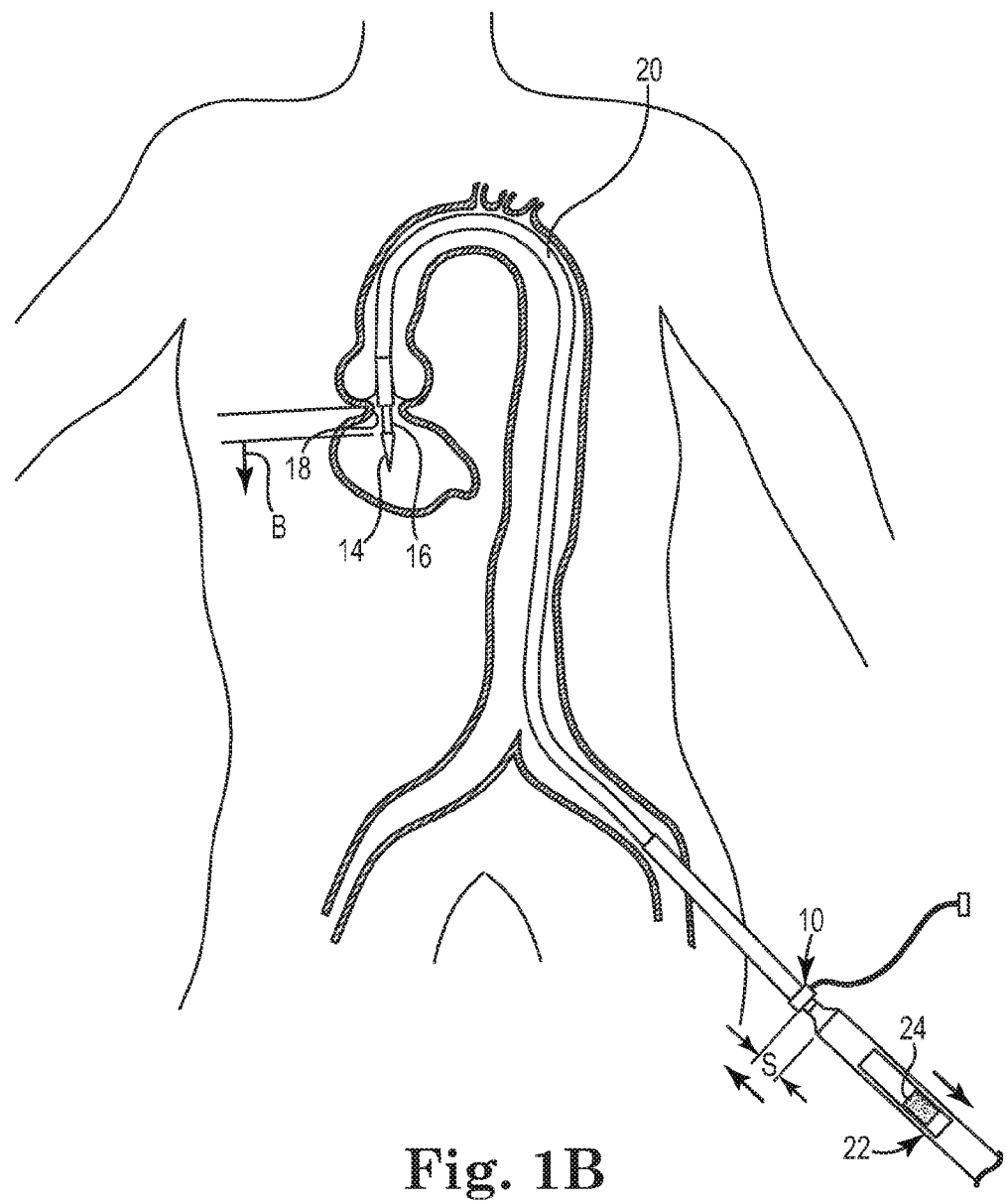

As referred to herein, stented transcatheter prosthetic heart valves useful with and/or as part of the various systems, devices, and methods of the present disclosure may assume a wide variety of different configurations, such as a bioprosthetic heart valve having tissue leaflets or a synthetic heart valve having polymeric, metallic, or tissue-engineered leaflets, and can be specifically configured for replacing any heart valve. Thus, the stented prosthetic heart valve useful with the systems, devices, and methods of the present disclosure can be generally used for replacement of a native aortic, mitral, pulmonic, or tricuspid valve, for use as a venous valve, or to replace a failed bioprosthesis, such as in the area of an aortic valve or mitral valve, for example.

In general terms, the stented prosthetic heart valves of the present disclosure include a stent or stent frame maintaining a valve structure (tissue or synthetic), with the stent having a normal, expanded arrangement and collapsible to a compressed arrangement for loading within a delivery device. The stent is normally constructed to self-deploy or self-expand when released from the delivery device. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems, devices, and methods of the present disclosure are described in U.S. Publication Nos. 2006/0265056; 2007/0239266; and 2007/0239269, the teachings of each which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a variety of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine pericardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaflets; however, replacement prosthetic heart valves of the types described herein can incorporate more or less than three leaflets.

Some embodiments of the stent frames can be a series of wires or wire segments arranged such that they are capable of self-transitioning from the compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the normal, expanded arrangement. In the compressed arrangement, such a stent frame support structure with attached valve leaflets can be mounted onto a delivery device. The stent frame support structures are configured so that they can be changed to their normal, expanded arrangement when desired, such as by the relative movement of one or more outer sheaths relative to a length of the stent frame.

The wires of these stent frame support structures in embodiments of the present disclosure can be formed from a shape memory material such as a nickel titanium alloy (e.g., Nitinol™). With this material, the support structure is self-expandable from the compressed arrangement to the normal, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery device that can be used includes a catheter with a retractable sheath that covers the stent frame until it is to be deployed, at which point the sheath can be refracted to allow the stent frame to self-expand. Further details of such embodiments are discussed below.

Figure 2A:
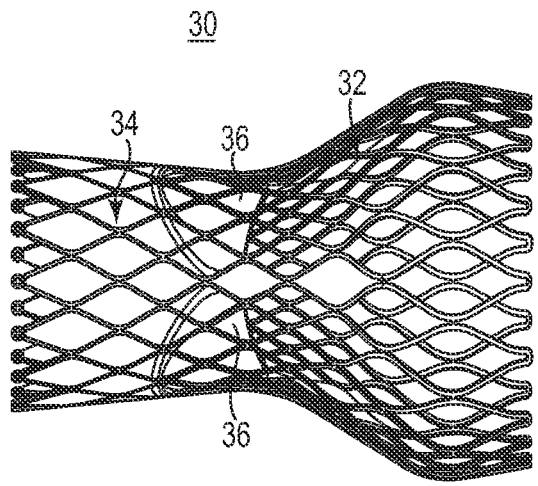
FIG. 2A is a side view of a stented prosthetic heart valve useful with systems, devices, and methods of the present disclosure and in a normal, expanded arrangement.
Figure 2B:
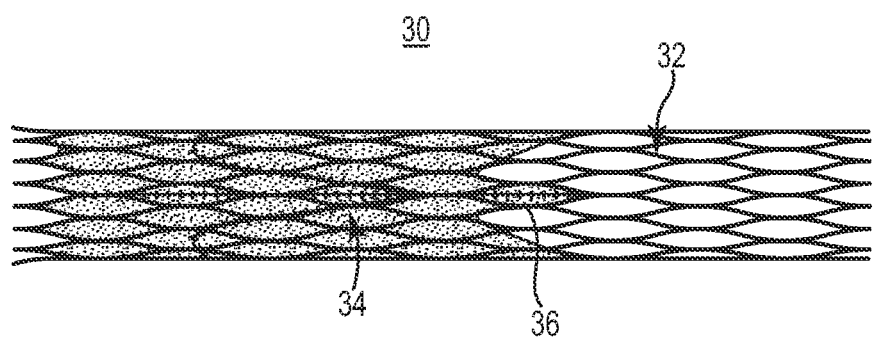
FIG. 2B is a side view of the prosthetic heart valve of FIG. 2A in a compressed arrangement.

With the above understanding in mind, one non-limiting example of a stented prosthetic heart valve 30 useful with systems, devices, and methods of the present disclosure is illustrated in FIG. 2A. As a point of reference, the prosthetic heart valve 30 is shown in a normal or expanded arrangement in the view of FIG. 2A; FIG. 2B illustrates the prosthetic heart valve 30 in a compressed arrangement (e.g., when compressively retained within an outer catheter or sheath). The prosthetic heart valve 30 includes a stent or stent frame 32 and a valve structure 34. The stent frame 32 can assume any of the forms described above, and is generally constructed so as to be self-expandable from the compressed arrangement (FIG. 2B) to the normal, expanded arrangement (FIG. 2A). In other embodiments, the stent frame 32 is expandable to the expanded arrangement by a separate device (e.g., a balloon internally located within the stent frame 32). The valve structure 34 is assembled to the stent frame 32 and provides two or more (typically three) leaflets 36. The valve structure 34 can assume any of the forms described above, and can be assembled to the stent frame 32 in various manners, such as by sewing the valve structure 34 to one or more of the wire segments defined by the stent frame 32.

With the but one acceptable construction of FIGS. 2A and 2B, the prosthetic heart valve 30 is configured for replacing or repairing an aortic valve. Alternatively, other shapes are also envisioned, adapted to the specific anatomy of the valve to be repaired (e.g., stented prosthetic heart valves in accordance with the present disclosure can be shaped and/or sized for replacing a native mitral, pulmonic, or tricuspid valve). With the one construction of FIGS. 2A and 2B, the valve structure 34 extends less than the entire length of the stent frame 32, but in other embodiments can extend along an entirety, or a near entirety, of a length of the stent frame 32. A wide variety of other constructions are also acceptable and within the scope of the present disclosure. For example, the stent frame 32 can have a more cylindrical shape in the normal, expanded arrangement.

With the above understanding of the stented prosthetic heart valve 30 in mind, one embodiment of a system 38 for restoring (e.g., replacing) a defective heart valve is shown in FIG. 3, and includes a delivery device 40 for percutaneously delivering and implanting the prosthetic heart valve 30. The delivery device 40 includes a delivery sheath assembly 42, an inner shaft assembly 44 (referenced generally), an outer stability tube 46, and a handle 48. Details on the various components are provided below. In general terms, however, the system 38 is transitionable from a loaded or delivery condition (shown in FIG. 3) in which the stented prosthetic heart valve (hidden in the view of FIG. 3) is contained within a capsule 50 of the delivery sheath assembly 42, to a deployed condition in which the capsule 50 is retracted from the prosthetic heart valve, thereby permitting the prosthetic heart valve to self-expand (or alternatively be caused to expand by a separate mechanism such as a balloon) and release from the delivery device 40. As part of this transitioning, the delivery sheath assembly 42 is slidable relative to the stability tube 46, with the stability tube 46 serving to frictionally isolate the delivery sheath assembly 42 from a separate introducer device (not shown). In some embodiments, in the delivery condition, the delivery device 40 is transitionable from a first delivery state (shown in FIG. 3) in which a distal region 52 of the stability tube 46 has a first, low profile diameter, to a second delivery state in which the distal region 52 has an increased diameter that can more readily slidably receive the capsule 50. With this construction, the first delivery state facilitates passage through the patient's vasculature, whereas the second delivery state allows the stability tube 46 to be closely positioned to the capsule 50, thereby desirably enhancing stabilization of the delivery sheath assembly 42. In other embodiments, the delivery device 40 is configured to effectuate transitioning of the distal region 52 upon retraction of the capsule 50 within the distal region 52.

Figure 4:
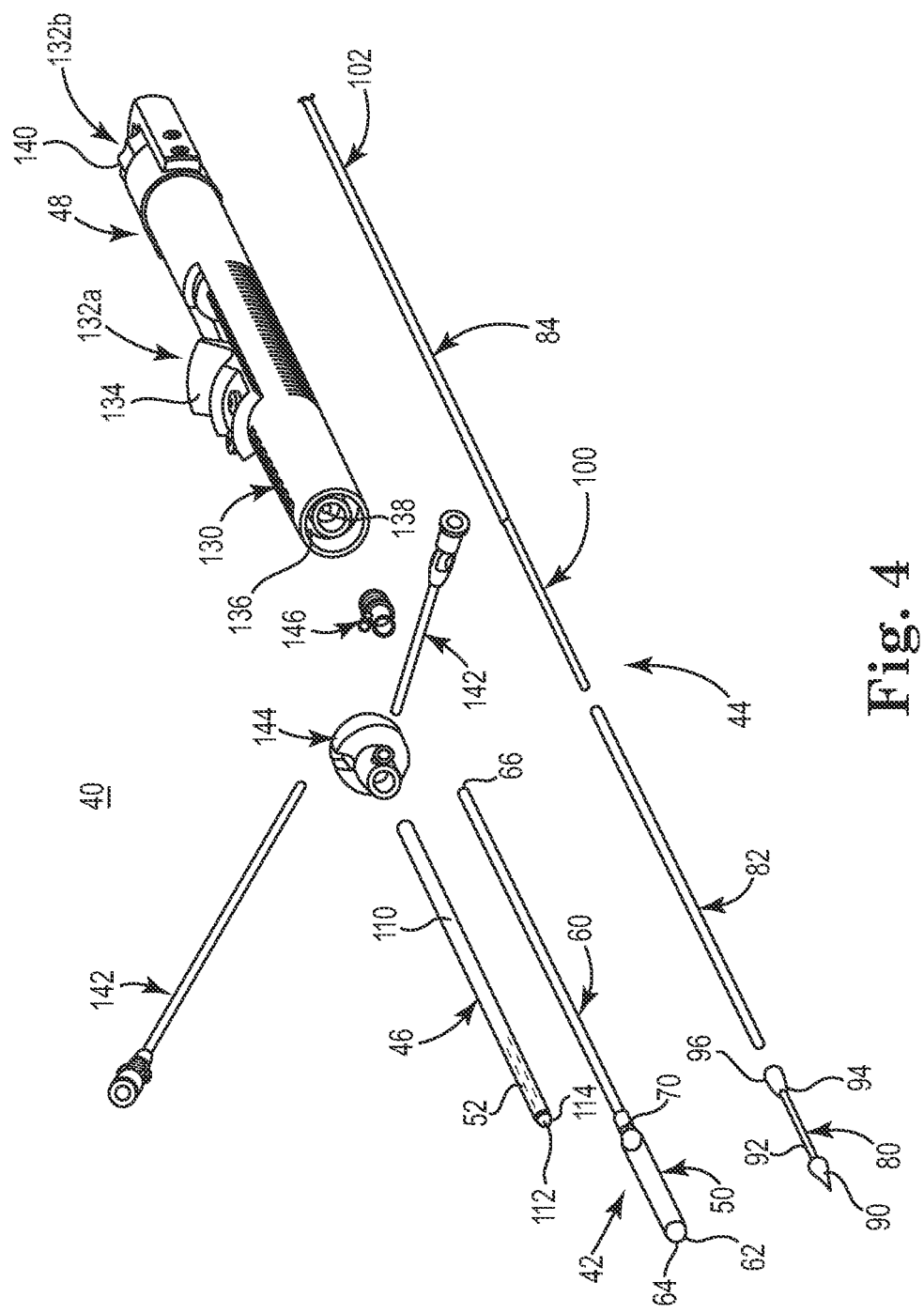
FIG. 4 is an exploded, perspective view of a delivery device portion of the system of FIG. 3.

Components in accordance with some embodiments of the delivery device 40 are shown in greater detail in FIG. 4. As a point of reference, various features of the components 42-48 reflected in FIG. 4 and described below can be modified or replaced with differing structures and/or mechanisms. Thus, the present disclosure is in no way limited to the delivery sheath assembly 42, the inner shaft assembly 44, the handle 48, etc., shown and described below. More generally, then, delivery devices in accordance with principles of the present disclosure provide features capable of compressively retaining a self-deploying stented prosthetic heart valve (e.g., the capsule 50), along with one or more components (e.g., the stability tube 46) capable of isolating the delivery sheath from an introducer device and having features that facilitate close positioning to the capsule 50.

In some embodiments, the delivery sheath assembly 42 includes the capsule 50 and a shaft 60, and defines a lumen 62 (referenced generally) extending from a distal end 64 to a proximal end 66. In some constructions, the capsule 50 and the shaft 60 are comprised of differing materials and/or constructions, with the capsule 50 having a longitudinal length approximating (e.g., slightly greater than) a length of the prosthetic heart valve 30 (FIG. 2B) to be used with the device 40. The capsule 50 is attached to, and extends distally from, the shaft 60 and in some embodiments has a more stiffened construction (as compared to a stiffness of the shaft 60) that exhibits sufficient radial or circumferential rigidity to overtly resist the expected expansive forces of the stented prosthetic heart valve 30 when compressed within the capsule 50. For example, the shaft 60 can be a polymer tube embedded with a metal braiding, whereas the capsule 50 includes a laser-cut metal tube that is optionally embedded within a polymer covering. Alternatively, the capsule 50 and the shaft 60 can have a more uniform construction (e.g., a continuous polymer tube). Regardless, the capsule 50 is constructed to compressively retain the stented prosthetic heart valve 30 at a predetermined diameter when loaded within the capsule 50, and the shaft 60 serves to connect the capsule 50 with the handle 48. To better accommodate a size of the compressed prosthesis 30 while at the same time maintaining an overall low profile, an outer diameter of the capsule 50 can be greater than an outer diameter of the shaft 60 in some embodiments. The shaft 60 (as well as the capsule 50) is constructed to be sufficiently flexible for passage through a patient's vasculature, yet exhibits sufficient longitudinal rigidity to effectuate desired axial movement of the capsule 50. In other words, proximal retraction of the shaft 60 is directly transferred to the capsule 50 and causes a corresponding proximal retraction of the capsule 50. In other embodiments, the shaft 60 is further configured to transmit a rotational force or movement onto the capsule 50.

The inner shaft assembly 44 can have various constructions appropriate for supporting a stented prosthetic heart valve within the capsule 50. For example, the inner shaft assembly 44 can include a retention member 80, an intermediate tube 82, and a proximal tube 84. In general terms, the retention member 80 is akin to a plunger, and incorporates features for retaining the stented prosthetic heart valve 30 (FIG. 2B) within the capsule 50 as described below. The intermediate tube 82 connects the retention member 80 to the proximal tube 84, with the proximal tube 84, in turn, coupling the inner shaft assembly 44 with the handle 48. The components 80-84 can combine to define a continuous lumen 86 (referenced generally) sized to slidably receive an auxiliary component such as a guide wire (not shown).

The retention member 80 can include a tip 90, a support tube 92, and a hub 94. The tip 90 forms or defines a nose cone having a distally tapering outer surface adapted to promote atraumatic contact with bodily tissue. The tip 90 can be fixed or slidable relative to the support tube 92. The support tube 92 extends proximally from the tip 90 and is configured to internally support a compressed, stented prosthetic heart valve generally disposed thereover, and has a length and outer diameter corresponding with dimensional attributes of the prosthetic heart valve 30 (FIG. 2B). The hub 94 is attached to the support tube 92 opposite the tip 90 (e.g., adhesive bond) and provides a coupling structure 96 (referenced generally) configured to selectively capture a corresponding feature of the prosthetic heart valve 30. The coupling structure 96 can assume various forms, and is generally located along an intermediate portion of the inner shaft assembly 44. In some embodiments, the coupling structure 96 includes one or more fingers sized to be slidably received within corresponding apertures formed by the prosthetic heart valve stent frame 32 (FIG. 2A). For example, the stent frame 32 can form wire loops at a proximal end thereof that are releasably received over respective ones of the fingers when compressed within the capsule 50. Other releasable coupling arrangements are also acceptable, such as the hub 94 forming one or more slots sized to slidably receive a corresponding component(s) of the prosthetic heart valve (e.g., a bar or leg segment of the stent frame 32 (FIG. 2B)). Further, the inner shaft assembly 44 can incorporate additional structures and/or mechanisms that assist in temporarily retaining the prosthetic heart valve (e.g., a tubular segment biased over the coupling structure 96), such as described in U.S. Provisional Application Ser. No. 61/237,373 entitled "Transcatheter Valve Delivery Systems and Methods" filed Aug. 27, 2009 and the entire teachings of which are incorporated herein by reference.

The intermediate tube 82 is formed of a flexible material (e.g., PEEK), and is sized to be slidably received within the delivery sheath assembly 42 and in particular the shaft 60. The proximal tube 84 can include a leading portion 100 and a trailing portion 102. The leading portion 100 serves as a transition between the intermediate and proximal tubes 82, 84, and thus can be a flexible tubing (e.g., PEEK) having a diameter slightly less than that of the intermediate tube 82. The trailing portion 102 has a more rigid construction, configured for robust assembly with the handle 48. For example, the trailing portion 102 can be a metal hypotube, although other constructions are also acceptable. In yet other embodiments, the intermediate and proximal tubes 82, 84 are integrally formed as a single, homogenous tube or solid shaft.

The stability tube 46 includes or defines the distal region 52 and a proximal region 110. The stability tube 46 forms a lumen 112 (referenced generally) sized to be slidably received over the delivery sheath assembly 42 as described below, with the stability tube 46 terminating at a distal end 114.

Figure 5A:
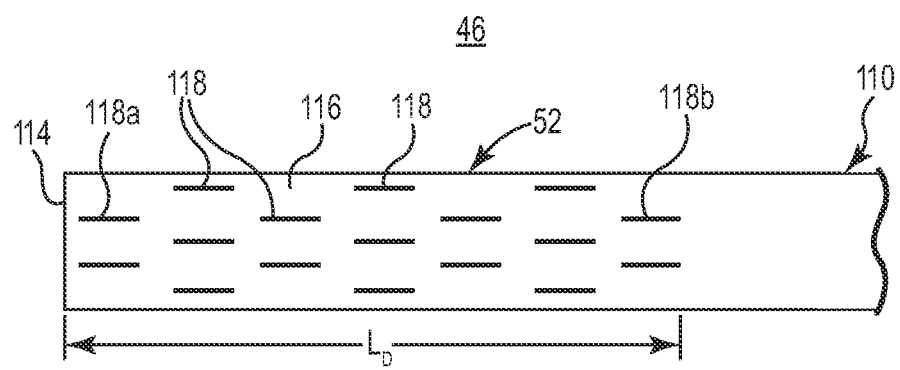
FIG. 5A is a side view of a distal region portion of a stability tube component of the delivery device of FIG. 4 in a first shape.
Figure 5B:
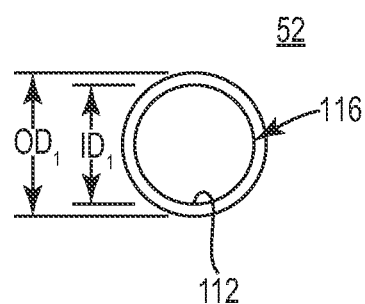
FIG. 5B is an end view of the distal region of FIG. 5A.

The distal region 52 is configured to be radially expandable (e.g., in response to an internally applied, radially expansive force) from a first shape generally reflected in FIG. 4 to a second shape having an increased diameter. In some embodiments, the distal region 52 is configured such that upon removal of the expansive force, the distal region 52 self-maintains the general shape and diameter of the second shape. For example, FIGS. 5A and 5B illustrate the distal region 52 in the first shape. As shown, the distal region 52 has a longitudinal length $L_D$ and is generally comprised of a tubular wall 116 having a plurality of cuts 118 formed through a thickness thereof in some embodiments. The tubular wall 116 can be formed from a biocompatible polymer material conventionally employed for catheter-type applications and exhibiting plastic or substantially plastic deformation characteristics (e.g., nylon, polyethylene, etc.). The plurality of cuts 118 are formed in a pattern about a circumference of the stability tube 46 along the distal region 52, and in some constructions are longitudinally elongated slits (in at least the first shape of the distal region 52). Other structures can be incorporated into the distal region 52 (e.g., a braided wire embedded into the polymer tubular wall 116). Regardless, in the first shape, the lumen 112 along the distal region 52 defines an inner diameter $ID_1$ of the distal region 52, with a thickness of the tubular wall 116 defining an outer diameter $OD_1$. The inner diameter $ID_1$ and the outer diameter $OD_1$ can be uniform along an entirety of the distal region 52, or alternatively can be characterized as nominal, minimum inner and maximum outer dimensions of the distal region 52. As a point of reference, the length $L_D$ of the distal region 52 can be defined as a longitudinal distance between the distal end 114 (or a distal-most cut 118a) and a proximal-most cut 118b. For reasons made clear below, the distal region length $L_D$ approximates, or is slightly greater than, a longitudinal length of the capsule 50 (FIG. 4) and thus of a longitudinal length of the prosthetic heart valve 30 (FIG. 2B) in the compressed arrangement.

In some embodiments, except for the cuts 118, the proximal region 110 can have a construction identical to that of the distal region 52 (e.g., the stability tube 46 is a continuous, homogenous tube). Alternatively, the regions 52, 110 can be differently constructed and subsequently assembled to one another. In yet other embodiments, one or more intermediate regions of varying construction are interposed between the distal and proximal regions 52, 110.

Figure 6A:
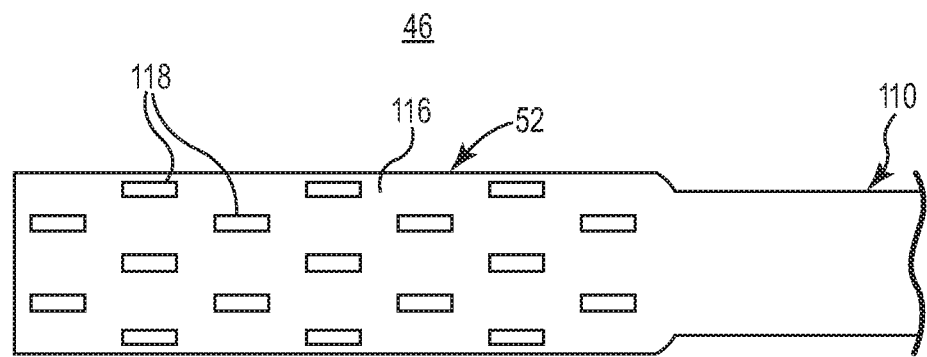
FIG. 6A is a side view of the distal region of FIG. 5A and in a second shape.
Figure 6B:
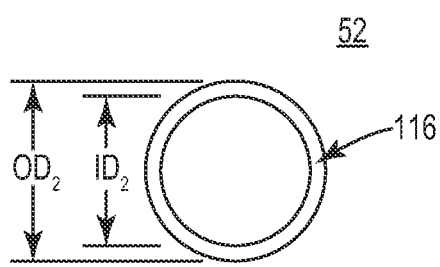
FIG. 6B is an end view of the stability tube of FIG. 6A.

By forming the plurality of cuts 118 as longitudinally elongated slits, a column strength of the distal region 52 is essentially the same as a column strength of the distal region 52 were the cuts 118 not formed (e.g., where the stability tube 46 is formed as a continuous, homogenous tube, the column strength of the distal and proximal regions 52, 110 is substantially the same). However, the cuts 118 permit the distal region 52 to readily expand to the second shape reflected, for example, in FIGS. 6A and 6B. In particular, when the distal region 52 is subjected to an internally expansive force, the tubular wall 116 will radially expand in diameter and deform, with the cuts 118 experiencing an increase in circumferential width. In some embodiments, the tubular wall 116 is configured to plastically or substantially plastically deform (e.g., within 10% of complete plastic deformation); in other embodiments, the distal region 52 elastically deforms. In the second shape of FIGS. 6A and 6B, then, the distal region 52 has an inner diameter $ID_2$ and an outer diameter $OD_2$ that are greater than the corresponding diameters $ID_1$, $OD_1$ (FIGS. 5A and 5B) of the first shape. Upon removal of the radially expansive force, the material and construction of the tubular wall 116 is such that the distal region 52 self-maintains the second shape. That is to say, due to the optional plastic or substantially plastic deformation property of the tubular wall 116 in some constructions, while the distal region 52 may slightly relax and radially retract upon removal of the internal expansive force, the expanded or stretched nature of the distal region 52 is substantially retained. Thus, the inner and outer diameters $ID_2$, $OD_2$ of the second shape are greater than the inner and outer diameters $ID_1$, $OD_1$ of the initial, first shape. For example, the distal region 52 can be configured such that upon removal of the radially expansive force, the distal region 52 retracts or relaxes in diameter by no more than 10%. Alternatively, the distal region 52 can exhibit elastic deformation properties, and will retract substantially back to the initial inner and outer diameters $ID_1$, $OD_1$ upon removal of the radially expansive force.

The radially expandable and optional shape retention features of the distal region 52 can be provided in a variety of other manners that may or may not include the cuts 118. For example, the distal region 52 can include one or more metal strips with shape memory characteristics embedded within a polymer tube; when subjected to a radially expansive force, the metal strips permit the polymer tube to expand, and then retain (or substantially retain) the so-imparted, expanded shape.

Returning to FIG. 4, the proximal region 110 connects the distal region 52 with the handle 48, and can thus be a polymer tube. In some constructions, the distal region 52 and the proximal region 110 are provided as a single, homogenous tube, with the cuts 118 (FIG. 5A) being formed therein to define the distal region 52 as described above. Regardless, the stability tube 46 serves as a stability shaft for the delivery sheath assembly 42, and has a length selected to extend over a significant (e.g., at least a majority), and in some embodiments at least 80%, of a length of the delivery sheath assembly 42 in distal extension from the handle 48. Further, the stability tube 46 exhibits sufficient radial flexibility to accommodate passage through a patient's vasculature (e.g., the femoral artery and the aortic arch).

The handle 48 generally includes a housing 130 and one or more actuator mechanisms 132 (referenced generally). The housing 130 maintains the actuator mechanism(s) 132, with the handle 48 configured to facilitate sliding movement of the delivery sheath assembly 42 relative to the inner shaft assembly 44 and the stability tube 46. Optionally, the handle 48 is further configured to facilitate sliding movement of the stability tube 46 relative to the delivery sheath assembly 42 and the inner shaft assembly 44. The housing 130 can have any shape or size appropriate for convenient handling by a user.

In one simplified construction, a first, deployment actuator mechanism 132a is provided and includes a user interface or actuator 134 slidably retained by the housing 130 and coupled to a delivery sheath connector body 136. The inner shaft assembly 44, and in particular the proximal tube 84, is slidably received within a passage 138 (referenced generally) of the delivery sheath connector body 136 and is rigidly coupled to the housing 130. A second, stability tube actuator mechanism 132b (referenced generally) is also provided and similarly includes a user interface or actuator 140 movably maintained by the housing 130 and coupled to the stability tube 46 via one or more bodies (not shown) facilitating movement of the stability tube 46 with operation of the stability tube actuator 140. With this but one acceptable construction, the deployment actuator 134 can be operated to effectuate axial or longitudinal movement of the delivery sheath assembly 42 relative to the inner shaft assembly 44 and the stability tube 46. Similarly, the stability tube actuator 140 can be manipulated to longitudinally or axially slide the stability tube 46 relative to the delivery sheath assembly 42 (and the inner shaft assembly 44). As implicated by the above, the actuator mechanisms 132a, 132b can assume various forms as would be apparent to one of skill. In yet other embodiments described below, the stability tube actuator mechanism 132b can be omitted. Further, the handle 48 can include other features, such as the optional port assemblies 142, cap 144, and/or manifold 146 as shown.

FIGS. 7A and 7B illustrate, in simplified form, a distal portion of the system 38 in the delivery condition, including the stented prosthetic heart valve 30 loaded within the delivery device 40 such that the delivery device 40 is in the delivery state. In the loaded or delivery condition of the system 38, the prosthetic heart valve 30 is crimped over the inner shaft assembly 44 such that the prosthetic heart valve 30 engages the coupling structure 96. The capsule 50 compressively contains the prosthetic heart valve 30 in the compressed arrangement. As shown, with the delivery device 40 construction of FIGS. 7A and 7B, an outer diameter $OD_C$ of the capsule 50 can be greater than an outer diameter $OD_S$ of the shaft 60 as may be necessary for optimally retaining the prosthetic heart valve 30 in the compressed arrangement. Finally, the stability tube 46 is coaxially arranged over the shaft 60 of the delivery sheath assembly 42, with the distal end 114 located proximal the capsule 50. As mentioned above, the distal region 52 can assume one of the two shapes in the delivery state of the device 40, with FIGS. 7A and 7B reflecting the first delivery state. More particularly, the distal region 52 assumes the first shape in the first delivery state, with the distal region inner diameter $ID_1$ approximating (e.g., within 5%) the outer diameter $OD_S$ of the shaft 60. The inner diameter of the proximal region 110 also approximates the shaft outer diameter $OD_S$, it being understood that a slight clearance (on the order of 1 French in some embodiments) can be provided. Thus, in the first delivery state, the inner diameter $ID_1$ of the distal region 52 is less than the capsule outer diameter $OD_C$. In some embodiments, the distal region outer diameter $OD_1$ (FIG. 5B) in the first delivery state is not greater than the capsule outer diameter $OD_C$, thereby providing an overall low profile attribute to the loaded delivery device 40. For example, in some embodiments, the capsule 50 and the distal region 52 (in the first shape) both have an outer diameter on the order of 16 French, although other dimensions are also acceptable.

The distal region 52 can be transitioned to the second shape by distally advancing the distal region 52 over the capsule 50 as shown in FIGS. 8A and 8B. Due to the circumferential rigidity of the capsule 50, as well as the resistance to radial compression provided by the loaded prosthetic heart valve 30, the capsule 50 exerts a radially expansive force onto the distal region 52. This force, in turn, causes the tubular wall 116 (FIG. 6B) of the distal region 52 to radially expand, with the plurality of cuts 118 facilitating this expansion. For example, and as described above, when subjected to an internally expansive force, the tubular wall 116 expands or deforms (optionally plastically or substantially plastically), with the cuts 118 increasing in circumferential width. As a point of reference, FIGS. 8A and 8B further reflect a comparison of the distal region length $L_D$ with a length $L_C$ of the capsule 50 and a length $L_P$ of the prosthesis 30. As shown, the distal region length $L_D$ can be slightly greater than the capsule length $L_C$ and the prosthesis length $L_P$, such that an entirety of the distal region 52 can be disposed over the capsule 50.

Upon subsequent retraction of the stability tube 46 relative to the delivery sheath assembly 42, the distal region 52 substantially self-maintains the expanded shape as reflected by the second delivery state of the delivery device 40 in FIGS. 9A and 9B. In particular, the distal end 114 of the stability tube 46 is located immediately proximal the capsule 50, with the distal region 52 having or maintaining the second shape described above. In this second delivery state, then, the distal region inner diameter $ID_2$ approximates (e.g., within 5%) the capsule outer diameter $OD_C$, such that the capsule 50 can subsequently be slidably received within the distal region lumen 112, for example during deployment of the prosthetic heart valve 30 as described below.

Figure 10:
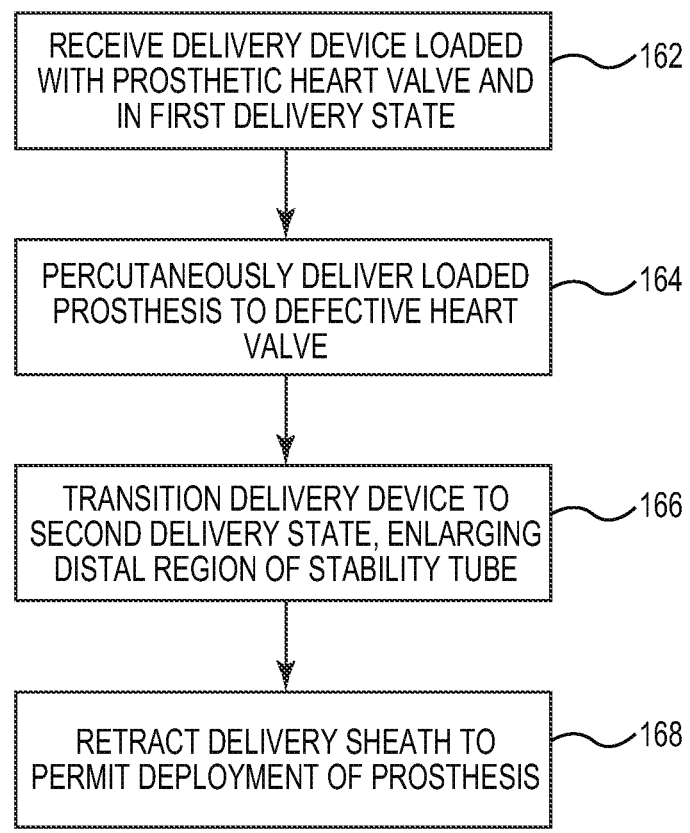
FIG. 10 is a flow diagram of a method for restoring (e.g., replacing) a defective heart valve in accordance with principles of the present disclosure.

With reference to the first delivery state (FIGS. 7A and 7B) and the flow diagram of FIG. 10, one method 160 for restoring (e.g., replacing) a defective heart valve begins at 162 in which a clinician receives the system 38 in the loaded or delivery condition, including the delivery device 40 arranged in the first delivery state. In particular, the stability tube 46 is arranged over the delivery sheath assembly shaft 60, with the distal region 52 assuming the first shape of FIGS. 7A and 7B. The delivery device 40 is then, at 164, manipulated to percutaneously deliver the prosthetic heart valve 30 (in the compressed arrangement) to a defective heart valve implantation site. For example, and with additional reference to FIG. 11A, the delivery device 40 can be used in conjunction with an introducer device 200. Introducer devices 200 are known in the art, and generally include an introducer sheath 202 and a valve 204. The introducer sheath 202 typically is a resilient body. To access a bodily lumen (e.g., femoral artery) of the patient, an incision 206 is formed in the patient's skin, and the introducer sheath 202 inserted through the incision 206 and into the desired bodily lumen. The valve 204 fluidly closes the connection with the bodily lumen external the patient. The delivery device 40 is then inserted into the bodily lumen via the introducer device 200. As generally reflected in FIG. 11A, for example, the introducer sheath 202 has an inner diameter greater than that of the outer stability tube 46 (as well as of the capsule 50), such that the capsule 50 can readily be delivered through the bodily lumen, directed to other branches of the patient's vasculature, and then to the defective heart valve implantation site 210 (e.g., aortic heart valve). In this regard, the introducer valve 204 frictionally contacts the stability tube 46, thereby establishing a low friction hemostasis seal around the stability tube 46. Notably, however, the stability tube 46 isolates the delivery sheath assembly 42 (in particular the shaft 60) from the introducer sheath 202 and the valve 204. Stated otherwise, while the stability tube 46 is in physical contact with portions of the introducer device 200, the delivery sheath assembly 42 does not directly contact the introducer device 200.

Figure 11A:
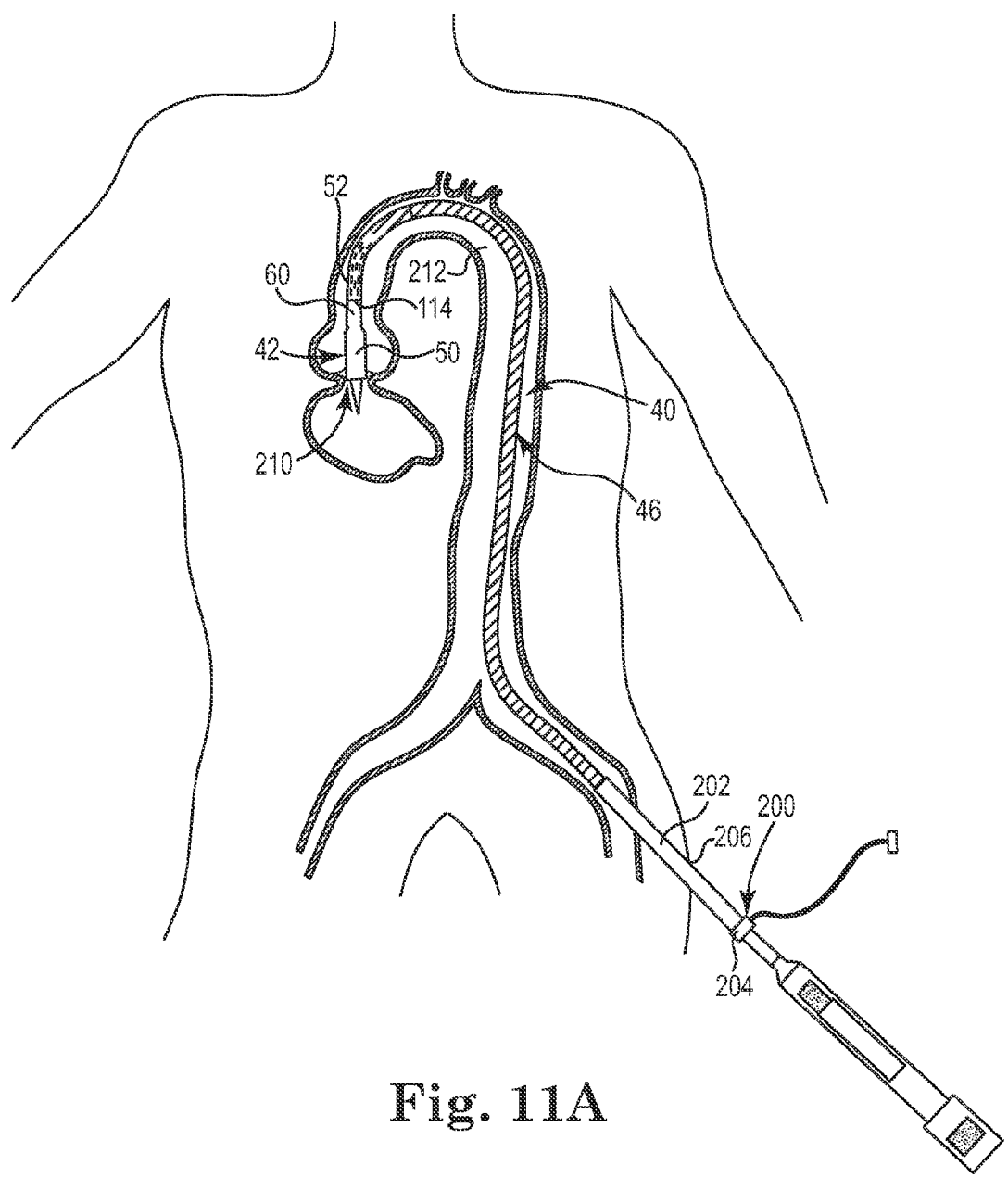
FIGS. 11A-11D illustrate various steps of the method of FIG. 10.

As further reflected in FIG. 11A, as part of the initial delivery step, the delivery device 40 has an overall low profile due to the distal region 52 of the stability tube 46 assuming the first shape. By optionally locating the distal end 114 of the stability tube 46 in close proximity to the capsule 50, the stability tube 46 overtly supports the delivery sheath assembly shaft 60 in traversing the tortuous vasculature, minimizing occurrences of kinks forming in the shaft 60 when, for example, moving across the aortic arch 212.

Figure 11B:
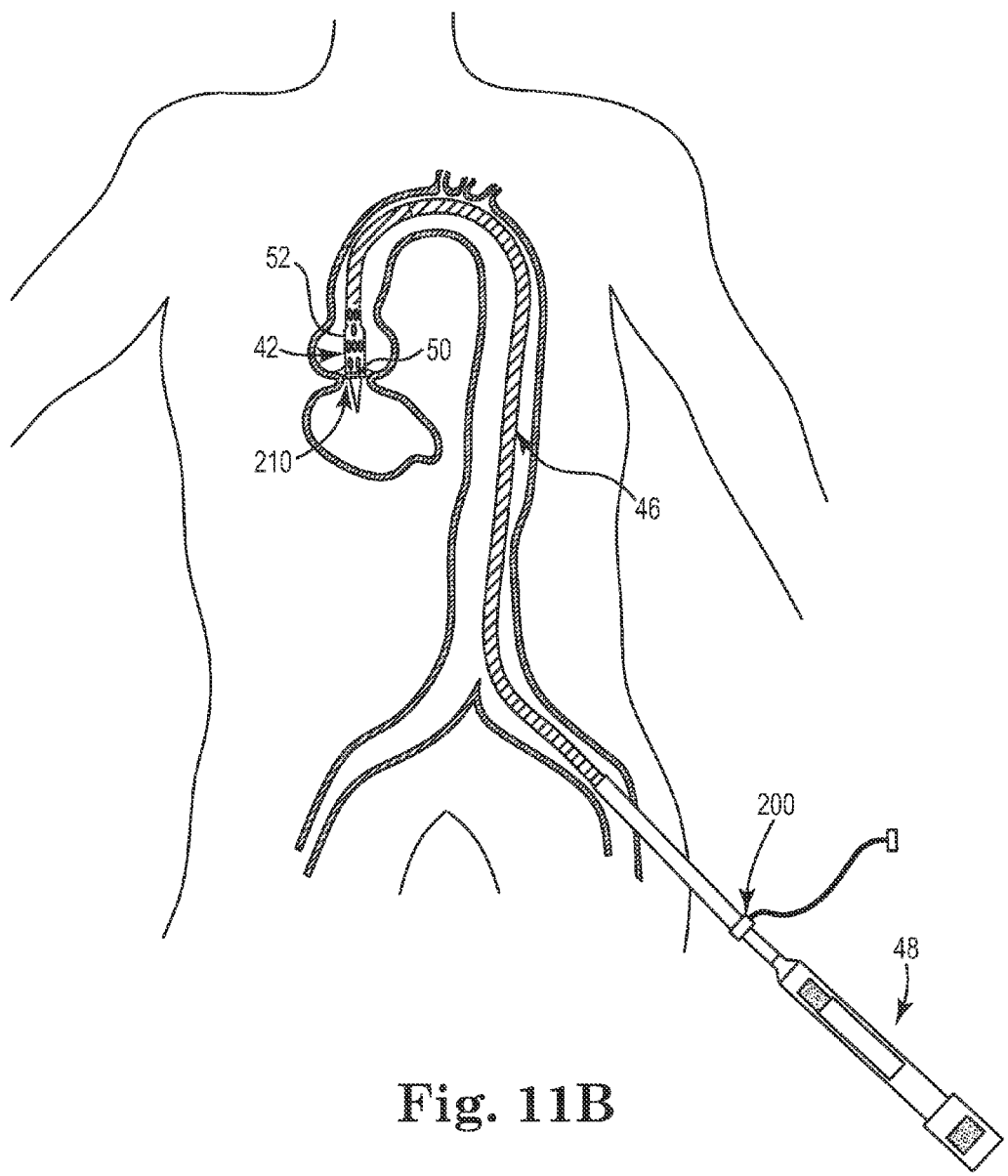
Figure 11C:
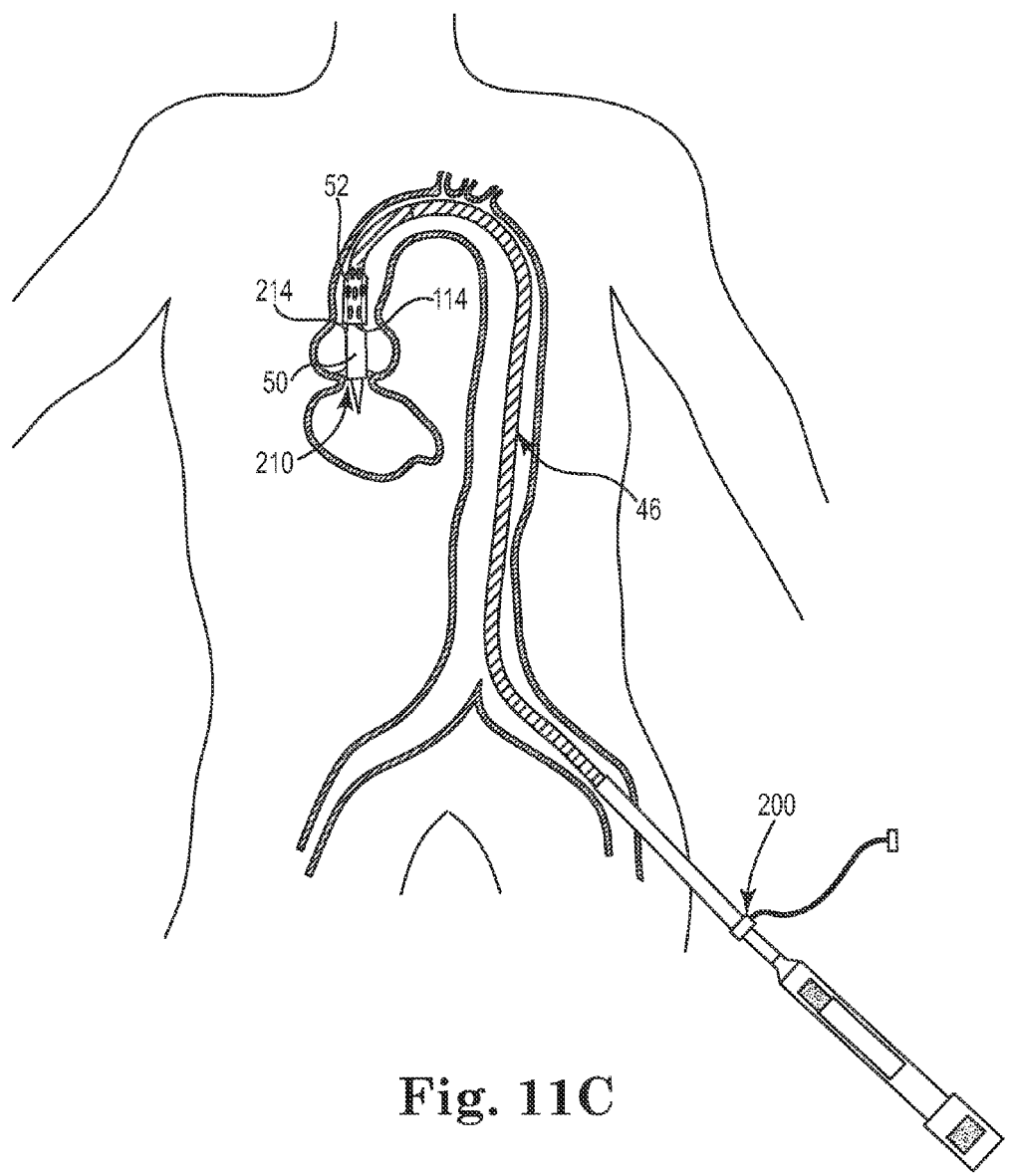

With reference between FIGS. 10 and 11B, at 166, the distal region 52 of the stability tube 46 is then transitioned to the second shape. For example, the handle 48 is operated to distally advance the stability tube 46 relative to the delivery sheath assembly 42 (referenced generally) such that the distal region 52 is disposed over the capsule 50 (referenced generally). As described above (FIGS. 8A and 8B), an interface between the distal region 52 and the capsule 50 (otherwise loaded over the prosthetic heart valve 30 (hidden in FIG. 11B)) causes the distal region 52 to plastically or substantially plastically expand. Subsequently, and as shown in FIG. 11C, the handle 48 is operated to retract the stability tube 46 proximally, thereby withdrawing the distal region 52 from the capsule 50. Thus, in the second delivery state of FIG. 11C, the distal region 52 self-maintains the second, expanded shape, with the distal end 114 being positioned immediately proximal the capsule 50. For example, a spacing between the distal end 114 of the stability tube 46 and a proximal end 214 of the capsule 50 can be less than the length $L_C$ (FIG. 8B) of the capsule 50, and less than the length of $L_P$ (FIG. 8B) of the prosthesis 30. In other embodiments, the distal end 114 can be immediately proximal the proximal end 214 of the capsule 50 (e.g., within 1 cm, alternatively within 0.5 cm).

Figure 11D:
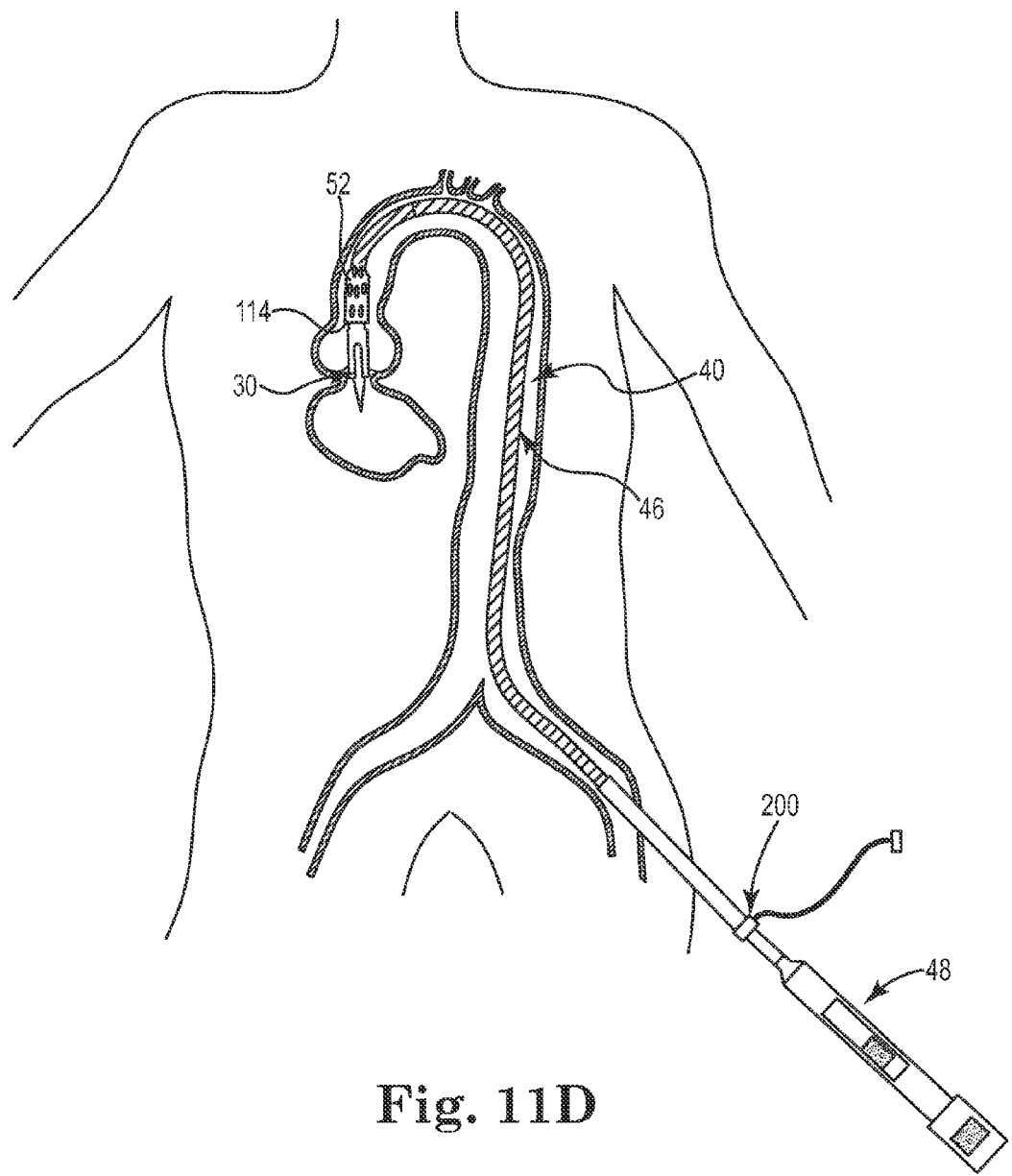

With cross-reference between FIGS. 10 and 11D, the handle 48 is operated to distally retract the delivery sheath assembly 42 (FIG. 4) at 168. In particular, the capsule 50 is withdrawn from over the prosthetic heart valve 30 (drawn schematically in FIG. 11D), thereby permitting the prosthetic heart valve 30 to self-deploy from the delivery device 40. In this regard, due to the presence of the stability tube 46, with transitioning of the delivery device 40 from the delivery state to the deployment state via sliding of the delivery sheath assembly 42 (hidden in FIG. 11D), the delivery sheath 42 does not bear against or otherwise frictionally interface with the introducer device 200. As a result, unlike previous percutaneous heart valve delivery procedures, the clinician and an assistant are not required to carefully monitor a spacing between the handle 48 and the introducer device 200 while constantly correcting any discrepancies as no frictional interface is established during retraction of the delivery sheath assembly 42. Further, because the distal end 114 of the stability tube 46 is in highly close proximity to the capsule 50 (FIG. 11C), an overall stabilization of the delivery sheath assembly 42 during retraction thereof is provided. Also, because the distal region 52 is in the expanded, second shape, the capsule 50 readily slides within the distal region 52 as shown in FIG. 11D. That is to say, because the distal region inner diameter $ID_2$ (FIG. 9B) in the second delivery state approximates the capsule outer diameter $OD_C$ (FIG. 9B), the distal end 114 of the stability tube 46 will not overtly abut against the capsule 50 in a manner that might otherwise impede necessary retraction of the capsule 50.

While the delivery device 40 has been described as transitioning the distal region 52 of the stability tube 46 from the first delivery state to the second delivery state via distal movement over the capsule 50, in other constructions the delivery device 40 is constructed such that the stability tube 46 remains stationary relative to the delivery sheath assembly 42 throughout the procedure. For example, an alternative system 300 for restoring (e.g., replacing) a defective heart valve is partially shown in FIG. 12A, and includes an alternative delivery device 302 in accordance with principles of the present disclosure loaded with a prosthetic heart valve 30 (hidden in the view of FIG. 12A). The delivery device 302 includes a delivery sheath assembly 304, an inner shaft assembly 306 (referenced generally), and a stability tube 308. Though not shown, the components 304-308 are proximally maintained by a handle. The handle is akin to the handle 48 (FIG. 4) described above, that need only provide a single actuator mechanism (i.e., the deployment actuator mechanism 132a (FIG. 4)) configured to effectuate user-caused movement of the delivery sheath assembly 304 relative to the inner shaft assembly 306 and the stability tube 308.

The delivery sheath assembly 304 can incorporate any of the constructions described above, and can be akin to the delivery sheath assembly 42 (FIG. 4). Thus, for example, the delivery sheath assembly 304 can include a distal capsule 310 and a proximal shaft 312. As with previous embodiments, the capsule 310 is configured to compressively contain a stented prosthetic heart valve (hidden), with the shaft 312 connecting the capsule 310 to the handle (not shown). The inner shaft assembly 306 can similarly assume any of the constructions described above, and thus can be akin to the inner shaft assembly 44 (FIG. 4). In more general terms, then, the inner shaft assembly 306 incorporates or includes one or more engagement features (not shown) configured to releasably engage the stented prosthetic heart valve otherwise disposed within the capsule 310.

The stability tube 308 is akin to the stability tube 46 (FIG. 4) described above, and includes a distal region 320 including a tubular body 322 terminating at a distal end 324 and having a plurality of cuts 326 formed through a thickness thereof. The distal region 322 is configured to be radially expandable from a first shape shown in FIG. 12A to a second, larger diameter shape described below. In this regard, a circumferential rigidity of the distal region 322 is less than a circumferential rigidity of the capsule 50 such that upon retraction of the capsule 50 into the distal region 322, the distal region 322 is forcibly expanded to the second shape.

Figure 12A:
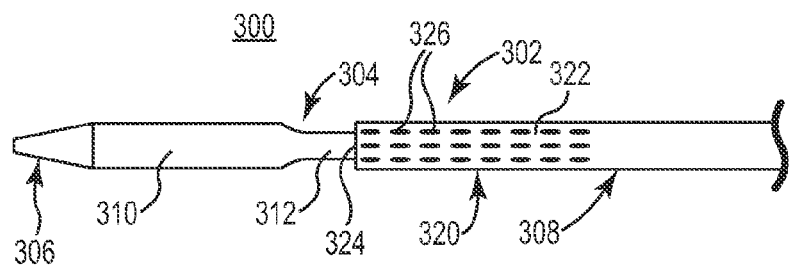
FIGS. 12A-12C illustrate a portion of another system for restoring (e.g., replacing) a defective heart valve, including an alternative delivery device in accordance with principles of the present disclosure.

In the delivery state or condition of FIG. 12A, the capsule 310 compressively retains the stented prosthetic heart valve (hidden in the view of FIG. 12A) in a compressed arrangement over the inner shaft assembly 306. The distal end 324 of the stability tube 308 is located proximal the capsule 310. The delivery device 302 can then be manipulated as described above to percutaneously deliver the stented prosthetic heart valve, in the compressed arrangement, to the heart valve to be restored.

Figure 12B:
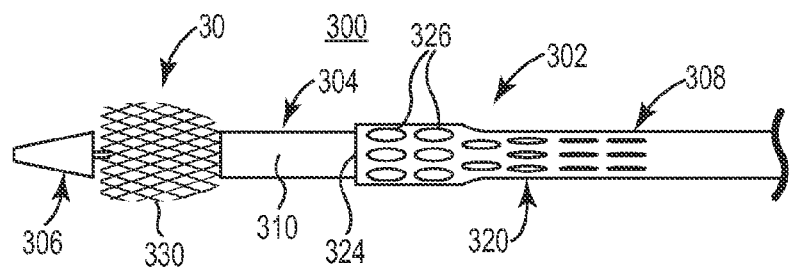

The delivery sheath assembly 304 can then be retracted to release the stented prosthetic heart valve (hidden in the view of FIG. 12A) from the confines of the capsule 310. For example, FIG. 12B illustrates the system 300 in a partially deployed condition, with the capsule 310 being partially refracted from the stented prosthetic heart valve 30. As shown, a distal portion 330 of the prosthesis 30 is exposed relative to the capsule 310 and has self-expanded toward the natural, expanded arrangement. A proximal region (hidden in FIG. 12B) remains within the capsule 310 and coupled to the inner shaft assembly 306. Further, as shown, the capsule 310 is partially withdrawn into the distal region 322 of the stability tube 308. In this regard, upon insertion of the capsule 310, the distal region 322 is forced to circumferentially expand to slidably accept the capsule 310, deforming to the second shape. In other words, because the capsule 310 is more circumferentially rigid than the distal region 322, as the capsule 310 is moved proximal the distal end 324, the corresponding segment of the distal region 322 deforms to the second shape. As with previous embodiments, each of the plurality of cuts 326 circumferentially expands in width in connection with this circumferential deformation.

Figure 12C:
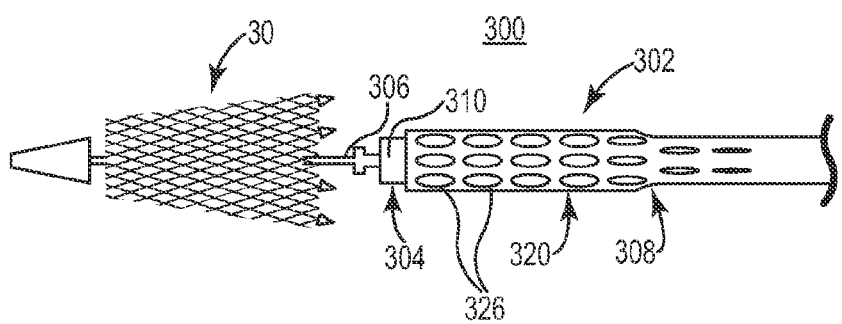

FIG. 12C illustrates the system 300 in a deployment condition, with the capsule 310 fully proximally retracted from over the stented prosthetic heart valve 30. As a result, the prosthetic heart valve 30 is free to self-expand toward the natural arrangement, and release from the delivery device 302. A substantial portion, and in some embodiments an entirety of, the capsule 310 is slidably disposed within the distal region 322 of the stability tube 308, with the distal region 322 readily transitioning to the second shape. As with previous embodiments, then, the distal end 324 of the stability tube 308 can be closely positioned to the capsule 310 prior to retraction (e.g., at a spacing that is less than a length of the capsule 310), thereby providing enhanced support.

Figure 13A:
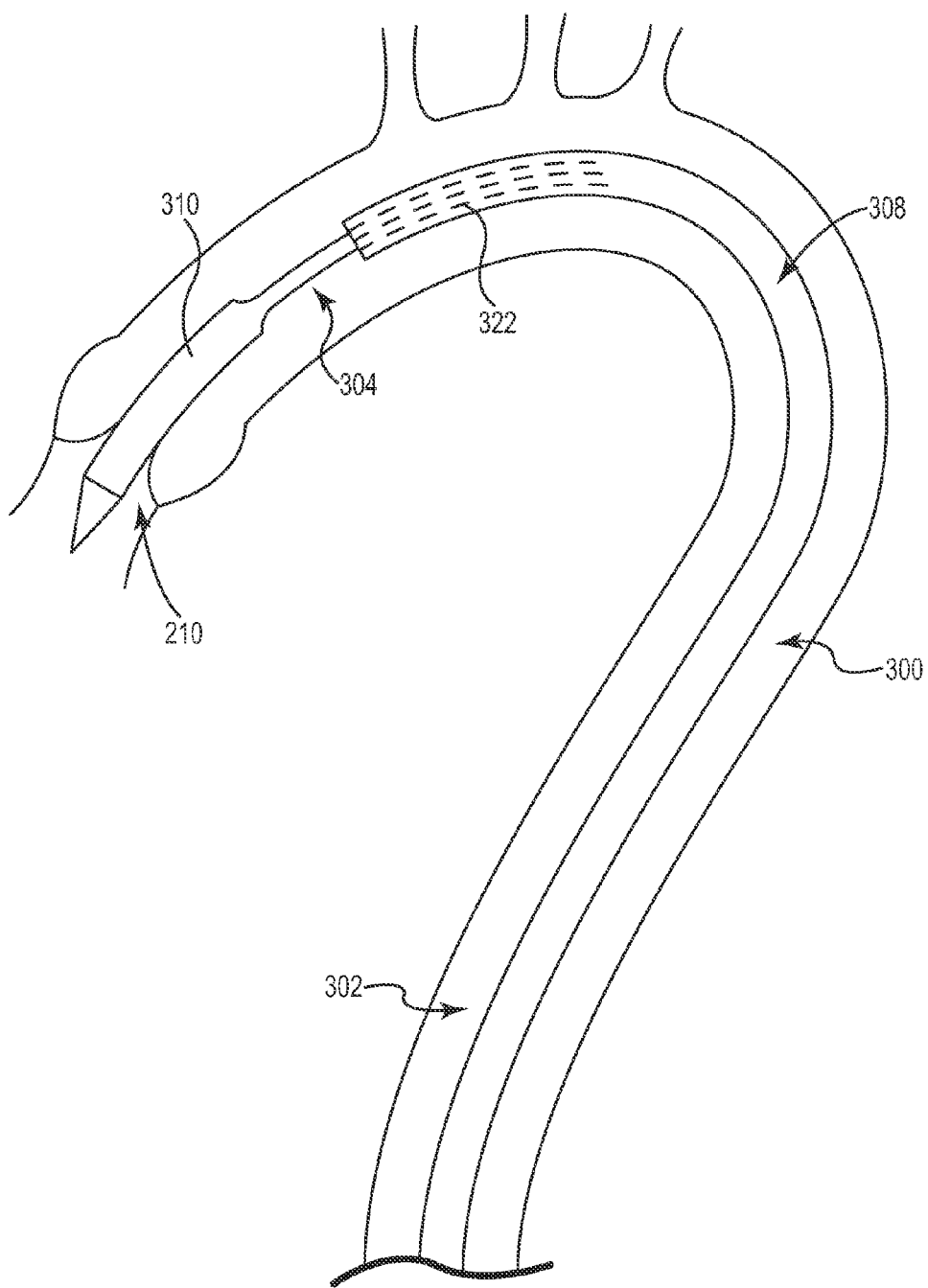
FIGS. 13A-13D illustrate, in simplified form, various steps of another method in accordance with principles of the present disclosure, including the systems of FIGS. 12A-12C.
Figure 13B:
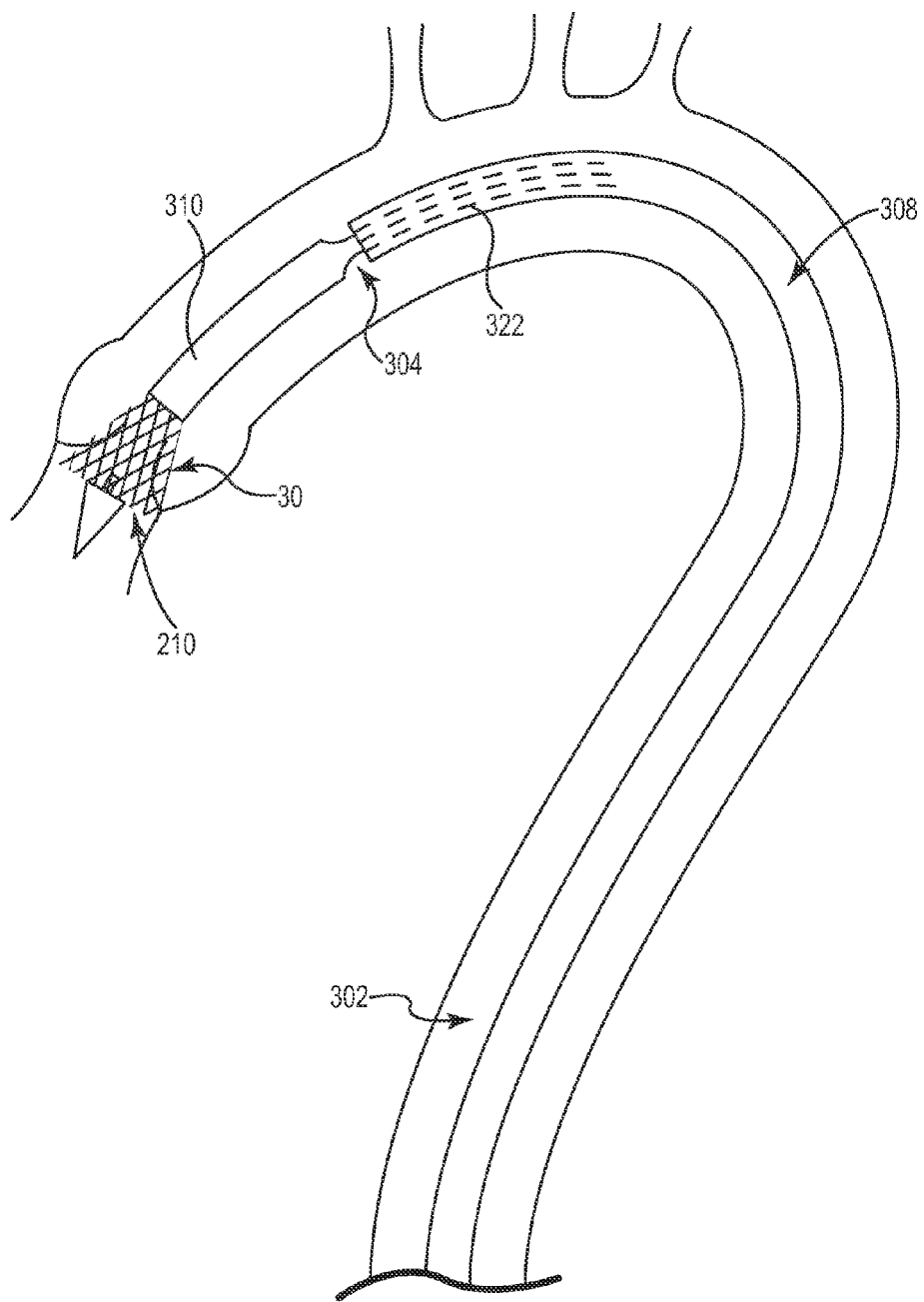
Figure 13C:
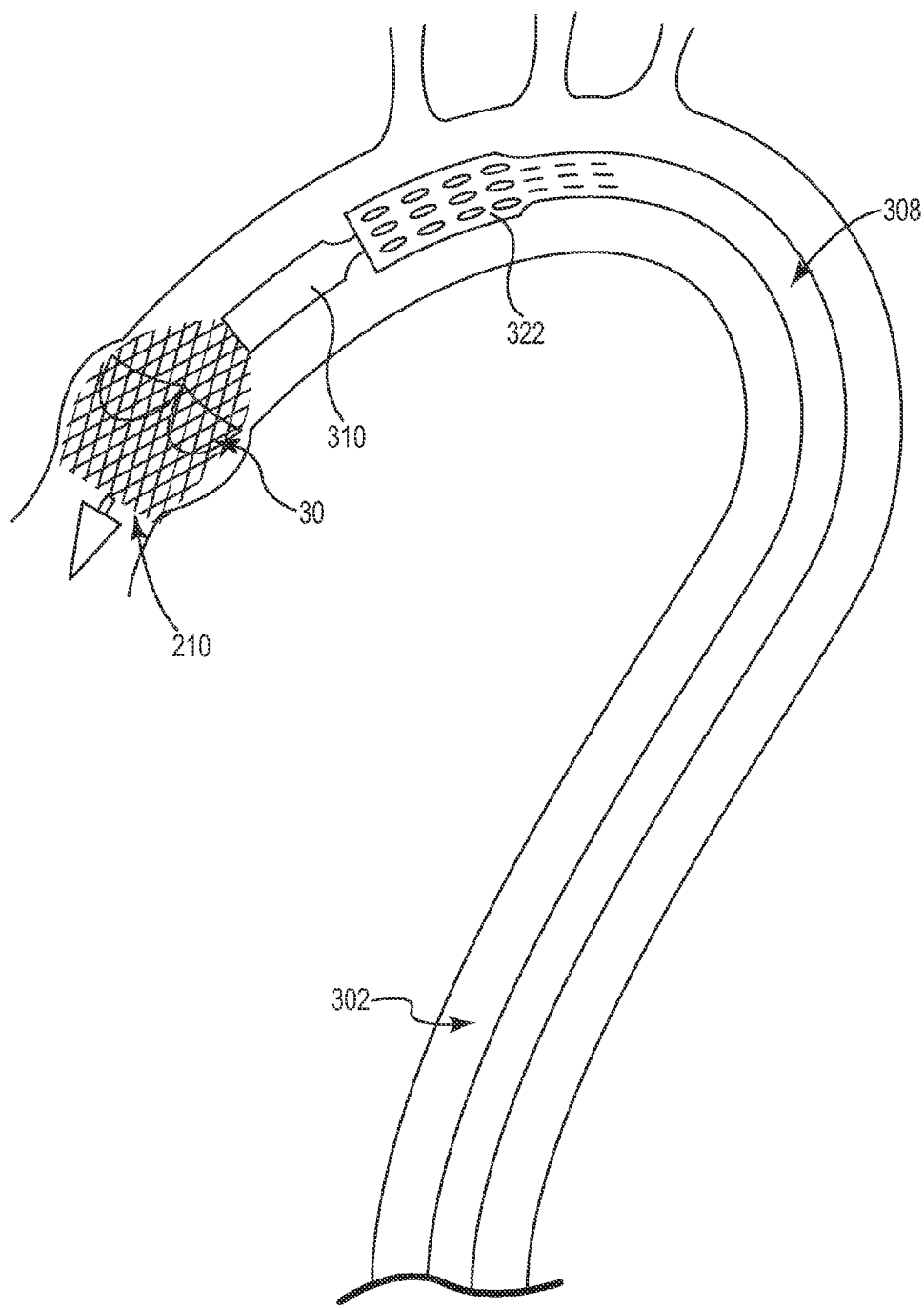
Figure 13D:
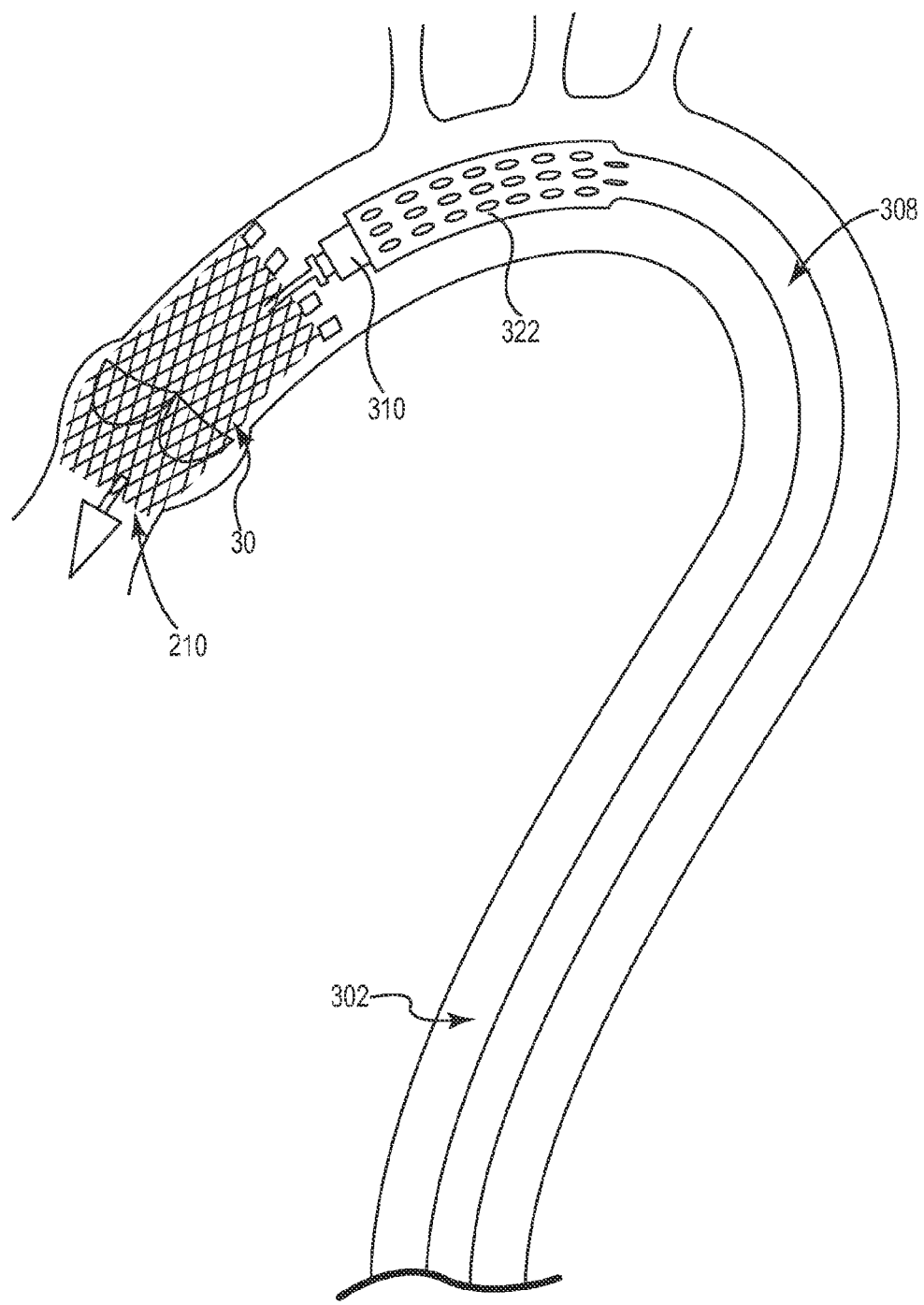

FIGS. 13A-13D illustrate, in simplified form, exemplary use of the system 300. The delivery device 302, in a deployment state, is manipulated to direct the stented prosthetic heart valve 30 (hidden in FIG. 13A) in the compressed arrangement to the implantation site 210 (FIG. 13A). The delivery sheath assembly 304 is then proximally withdrawn to retract the capsule 310 from the prosthesis 30, thereby allowing the prosthesis 30 to self-expand as in FIGS. 13B and 13C. The stability tube 308 remains stationary, with the capsule 310 being withdrawn into the distal region 322 and causing the distal region 322 to circumferentially expand or deform as shown in FIG. 13C. Upon full retraction of the capsule 310 from the stented prosthetic heart valve 30 (FIG. 13D), a substantial portion of the capsule 310 is within the distal region 322, with the distal region 322 transitioning to the second shape.

The stented prosthetic heart valve delivery systems, devices, and methods of the present disclosure provide a marked improvement over previous designs. By isolating the delivery sheath from the introducer device, potential complications associated with previous configurations are overcome. Further, by incorporating an expandable feature into the outer stability tube, low profile delivery followed by fully supported retraction of the delivery sheath is provided.

Although the present disclosure has been described with reference to preferred embodiments, workers skilled in the art will recognize that changes can be made in form and detail without departing from the spirit and scope of the present disclosure. For example, the delivery systems shown and described herein can be modified for delivery of balloon-expandable stented prosthetic heart valves, within the scope of the present disclosure. That is to say, delivering balloon-expandable stents to an implantation location can be performed percutaneously using modified versions of the delivery devices of the present disclosure. In general terms, this includes providing a transcatheter assembly that can include a delivery sheath and/or additional sheaths as described above. The devices would further include a delivery catheter, a balloon catheter, and/or a guide wire. A delivery catheter used in this type of delivery device defines a lumen within which the balloon catheter is received. The balloon catheter, in turn, defines a lumen within which the guide wire is slidably disposed. Further, the balloon catheter includes a balloon that is fluidly connected to an inflation source. With the stented valve mounted to the balloon, the transcatheter prosthetic valve is delivered through a percutaneous opening in the patient via the delivery device. Once the stented prosthetic heart valve is properly positioned, the balloon catheter is operated to inflate the balloon, thus transitioning the stented prosthesis to an expanded arrangement.

What is claimed is:

1. A delivery device for percutaneously delivering a stented prosthetic heart valve, the prosthetic heart valve being radially self-expandable from a compressed arrangement to a normal, expanded arrangement, the delivery device comprising:
   an inner shaft assembly including a coupling structure configured to selectively engage a stented prosthetic heart valve;
   a delivery sheath assembly slidably disposed over the inner shaft assembly and including a distal capsule and a proximal shaft, wherein the capsule is circumferentially rigid and is configured to compressively contain a stented prosthetic heart valve in a compressed arrangement;

an outer stability tube slidably disposed over the delivery sheath assembly, the stability tube including a proximal region and a distal region, the distal region including a tubular wall configured to be radially expandable from a first shape having a first diameter to a second shape having a second diameter, the second diameter being greater than the first diameter; and a handle including a housing maintaining the inner shaft assembly, the delivery sheath assembly and the stability tube, the handle being operable to selectively move the delivery sheath assembly relative to the inner shaft assembly and the stability tube;

wherein the delivery device is configured to provide a first delivery state in which the coupling structure is positioned within the capsule and the distal region is proximal the capsule and in the first shape, and a deployed state in which the capsule is at least partially withdrawn into the distal region and the distal region is in the second shape;

and further wherein the delivery device is configured such that from the first delivery state, the distal region is caused to radially expand from the first shape to the second shape solely in response to locating the capsule within the distal region.

2. The delivery device of claim 1, wherein an outer diameter of the capsule is greater than an outer diameter of the shaft, and further wherein an inner diameter of the distal region in the first shape approximates the outer diameter of the shaft.

3. The delivery device of claim 2, wherein the outer diameter of the distal region in the first shape is not greater than the outer diameter of the capsule.

4. The delivery device of claim 1, wherein the coupling structure includes at least one finger sized to selectively engage the stented prosthetic heart valve.

5. The delivery device of claim 1, wherein the distal region is configured to self-maintain the second shape upon transitioning from the first shape, and further wherein the delivery device is configured to provide a second delivery state in which the distal region is proximal the capsule and in the second shape, the second shape being sized to receive the capsule.

6. The delivery device of claim 5, wherein the delivery device is configured to transition from the first delivery state to the second delivery state by:
advancing the stability tube relative to the delivery sheath assembly such that the distal region is coaxially disposed over the capsule; and
subsequently retracting the stability tube relative to the delivery sheath assembly such that the distal region is proximal the capsule;
wherein an interface of the distal region with the capsule causes the distal region to transition to the second shape, the distal region maintaining the second shape when retracted from the capsule.

7. The delivery device of claim 5, wherein the handle is further configured to be operable to selectively move the stability tube relative to the delivery sheath assembly and the inner shaft assembly.

8. The delivery device of claim 1, wherein the distal region includes a plurality of cuts through a thickness of the tubular wall, and further wherein each of the plurality of cuts are longitudinally elongated.

9. The delivery device of claim 8, wherein the plurality of cuts expand in circumferential width in transitioning from the first shape to the second shape.

10. The delivery device of claim 1, wherein the distal region includes a plurality of cuts through a thickness of the tubular wall, and further wherein the plurality of cuts includes a distal-most cut and a proximal-most cut, and further wherein a longitudinal distance between the distal-most cut and the proximal-most cut is greater than a longitudinal length of the capsule.

11. The delivery device of claim 1, wherein the distal region includes a plurality of cuts through a thickness of the tubular wall, and further wherein the plurality of cuts are arranged in a pattern about a circumference of the distal region.

12. The delivery device of claim 1, wherein the distal region is caused to radially expand from the first shape to the second shape without any assistance of the stented prosthetic heart valve.

13. The delivery device of claim 12, wherein a column strength of the distal region and a column strength of the proximal region are substantially equal.

14. The delivery device of claim 12, wherein the outer stability tube is a polymer tube.

* * * * *